(12) United States Patent
Yamaguchi et al.

(10) Patent No.: US 7,537,340 B2
(45) Date of Patent: May 26, 2009

(54) OPHTHALMOLOGIC IMAGING APPARATUS

(75) Inventors: Tatsuo Yamaguchi, Tokyo (JP);
Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 90 days.

(21) Appl. No.: 11/697,000

(22) Filed: Apr. 5, 2007

(65) Prior Publication Data

US 2007/0236659 A1  Oct. 11, 2007

(30) Foreign Application Priority Data

Apr. 7, 2006 (JP) .............................. 2006-105934

(51) Int. Cl.
*A61B 3/10* (2006.01)
(52) U.S. Cl. ...................................... 351/205; 351/221
(58) Field of Classification Search ................... 351/205, 351/221
See application file for complete search history.

(56) References Cited

U.S. PATENT DOCUMENTS

2005/0286018 A1    12/2005  Yamaguchi et al.
2006/0146285 A1*   7/2006   Hirohara et al. ............. 351/221
2007/0030447 A1    2/2007   Yamaguchi et al.

FOREIGN PATENT DOCUMENTS

| JP | 2004-113405 A | 4/2004 |
|----|---------------|--------|
| JP | 2004-159779 A | 6/2004 |
| JP | 2004-159784 A | 6/2004 |
| JP | 2004-329282 A | 11/2004 |
| JP | 2006-6362 A   | 1/2006 |

* cited by examiner

*Primary Examiner*—Jordan M. Schwartz
*Assistant Examiner*—James C Jones
(74) *Attorney, Agent, or Firm*—Foley & Lardner LLP

(57) ABSTRACT

A pulse light source section outputs a plurality of pulse light according to the exposure timing of a retina imaging device. A retina illumination system illuminates the retina of an eye under measurement with the pulse light. A wavefront compensation system illuminates the eye and measures aberrations from a light reflected from the eye. The wavefront compensation system uses a wavefront compensation device and other components to compensate to cancel out measured aberrations. A retina imaging device receives a light which was reflected from the retina and of which the aberrations have been compensated for. A retina observation system forms an image of the retina on the retina imaging device with a light which was reflected and compensated. With the plurality of pulse light output from the pulse light source section, a plurality of consecutive retina images are obtained.

7 Claims, 20 Drawing Sheets

ABERRATION COMPENSATION FLOWCHART

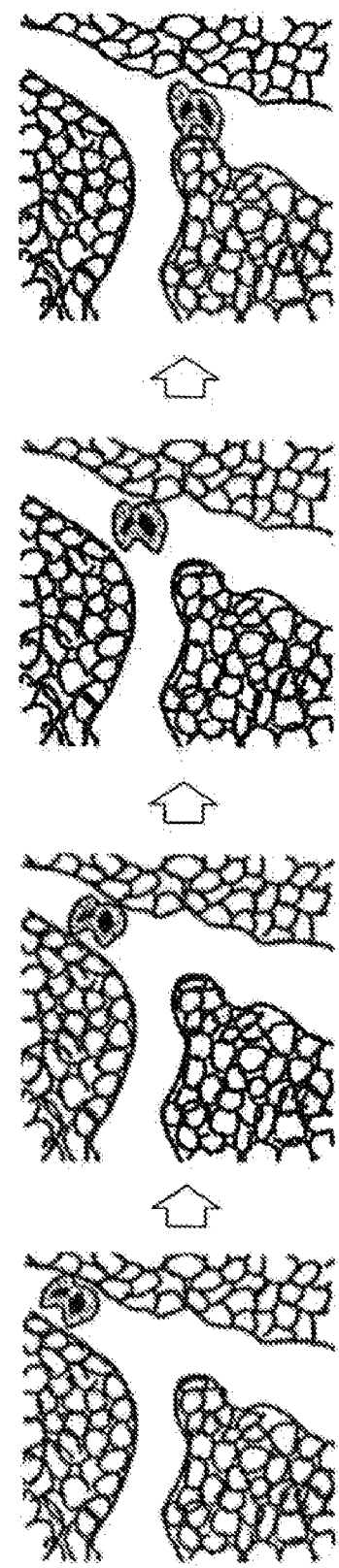
FIG. 7

TIMING CHART

RETINA ALIGNMENT FLOWCHART

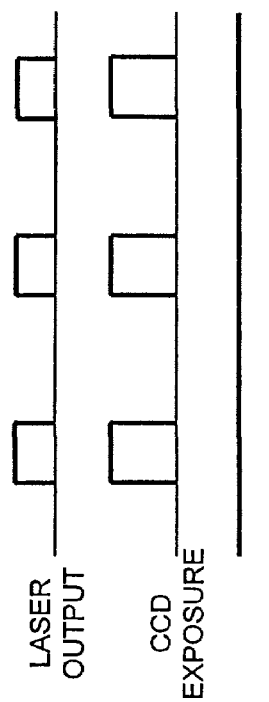
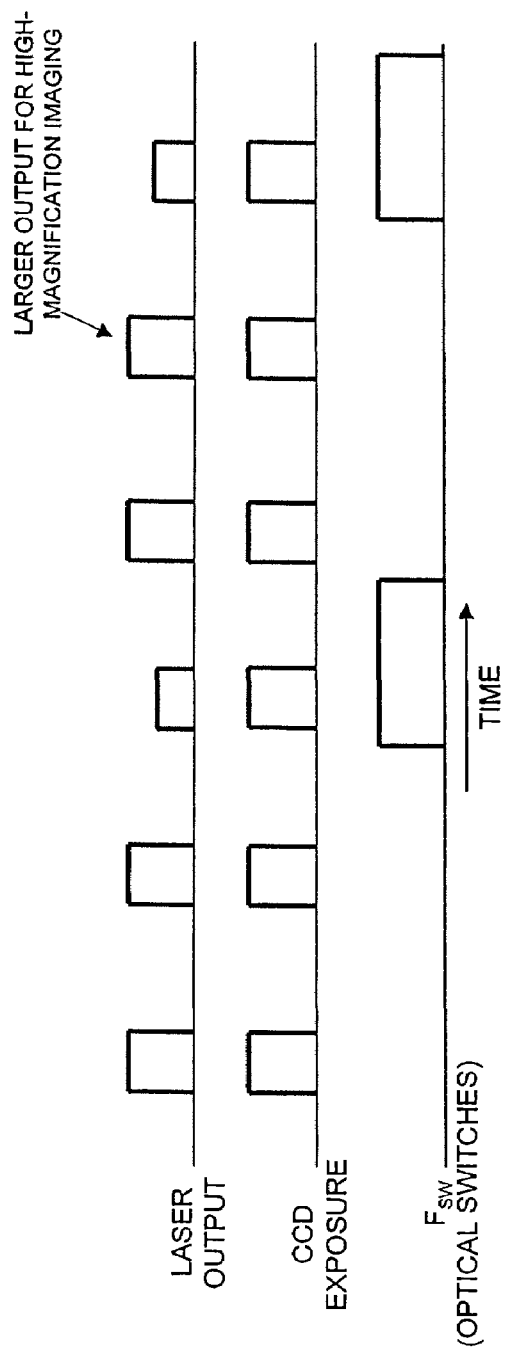

OPHTHALMOLOGIC IMAGING APPARATUS

BACKGROUND OF THE INVENTION

1. Field of the Invention

The present invention relates to ophthalmologic imaging apparatuses, and more particularly, to an ophthalmologic imaging apparatus for obtaining consecutive still images having small aberrations by pulse light emission.

2. Description of the Related Art

Only eyes include blood vessels which can be directly viewed without any surgical operations in a body. If a white blood cell can be observed in a blood flow, it helps to find general disorders such as diabetes. Since the size of a white blood cell is about 10 µm, however, it is difficult for current retina cameras to measure it. It is also very difficult to take moving images of a blood flow because the amount of light which can be allowed to be incident on an eye is restricted and the line of sight is not stable.

The following technologies have been disclosed by the assignee of present application. An eye-characteristic measurement apparatus which compensates for aberrations of an eye under measurement by a compensation optical section and measures precisely a minute aberration remaining after compensation is disclosed, for example, in Japanese Unexamined Patent Application Publication No. 2004-113405, No. 2004-159779, and No. 2004-159784. A retina observation apparatus which compensates a light beam reflected by an eye under measurement in order to improve retina-image quality and obtains an optimal image is disclosed, for example, in Japanese Unexamined Patent Application Publication No. 2004-329282. A retina-image observation apparatus which detects a displacement of an eye under measurement and moves a wavefront compensation device according to the detected shift position to compensate the wavefront is disclosed, for example, in Japanese Unexamined Patent Application Publication No. 2006-006362.

In a conventional optical apparatus, for example, a light source of continuous wave (CW) oscillation is used to illuminate a retina, which is continuous illumination. As a result, illumination is applied even for periods other than exposure periods. Since a load is imposed on a patient, long imaging is impossible in some cases. In addition, with an apparatus which uses adaptive optics, since an exposure period is generally long, a moving object causes a blurred image. Further, since an image is also taken in a case when aberrations are not compensated for, a separate process for classifying images is required to obtain successful images.

SUMMARY OF THE INVENTION

Accordingly, it is an object of the present invention to provide an ophthalmologic imaging apparatus capable of obtaining successful retina images for a long period of time. Another object of the present invention is to provide an ophthalmologic imaging apparatus capable of consecutively taking still images of fast-moving cells such as white blood cells. Another object of the present invention is to provide an ophthalmologic imaging apparatus that synchronizes light emission of a light source with an exposure signal for an imaging device, measures and compensates for aberrations in real-time, and controls the light emission of the light source so as to illuminate an eye under measurement when the aberrations are small.

According to the solving means of this invention, there is provided an ophthalmologic imaging apparatus comprising:

a light source section for emitting a pulse light at predetermined timing;

an illumination optical system for illuminating a retina of an eye under measurement, with the pulse light emitted from the light source section;

an aberration compensation section for applying compensation to a light beam reflected from the retina so as to cancel out at least high-order aberrations, according to measured aberrations;

an aberration measurement section for illuminating the eye under measurement, for receiving a light beam reflected from the eye under measurement when illuminated, through the aberration compensation section, and for measuring aberrations in the light beam reflected;

a light-receiving section for receiving a light beam coming from the retina to form an image; and a light-receiving optical system for forming a retina image on the light-receiving section with a light beam of the light source section, which was reflected from the retina and of which aberrations have been compensated for by the aberration compensation section, wherein the light source section emits a plurality of pulse lights at each exposure timing when the light-receiving section is exposed to light a plurality of times and the light-receiving section obtains consecutive retina images.

According to the present invention, it can provide an ophthalmologic imaging apparatus capable of obtaining successful retina images for a long period of time. According to the present invention, it can provide an ophthalmologic imaging apparatus capable of consecutively taking still images of fast-moving cells such as white blood cells. According to the present invention it can provide an ophthalmologic imaging apparatus that synchronizes light emission of a light source with an exposure signal for an imaging device, measures and compensates for aberrations in real-time, and controls the light emission of the light source so as to illuminate an eye under measurement when the aberrations are small.

BRIEF DESCRIPTION OF THE DRAWINGS

FIG. 7 is a view showing retina images taken in the first embodiment.

FIG. 17A and FIG. 17B are timing charts in the second embodiment.

DESCRIPTION OF THE PREFERRED EMBODIMENTS

1. First Embodiment

1.1 Outline

The present embodiment relates to an adaptive optics apparatus that synchronizes a pulse light source with a shutter for an imaging device to be capable of obtaining consecutive still images, for example, for observing the movement of a white blood cell. A retina camera that employs adaptive optics is used, the pulse light source performs pulse oscillation at about 500 μs or less, and the pulse oscillation is synchronized with the exposure period or the shutter of the imaging device (CCD in general) to make it possible to obtain successful images which show the movement of a white blood cell. Aberration compensation is performed in parallel, and light emission of the light source is controlled according to the state of the aberration compensation to allow successful images to be obtained.

1.2 Optical Arrangement

Figure 1:
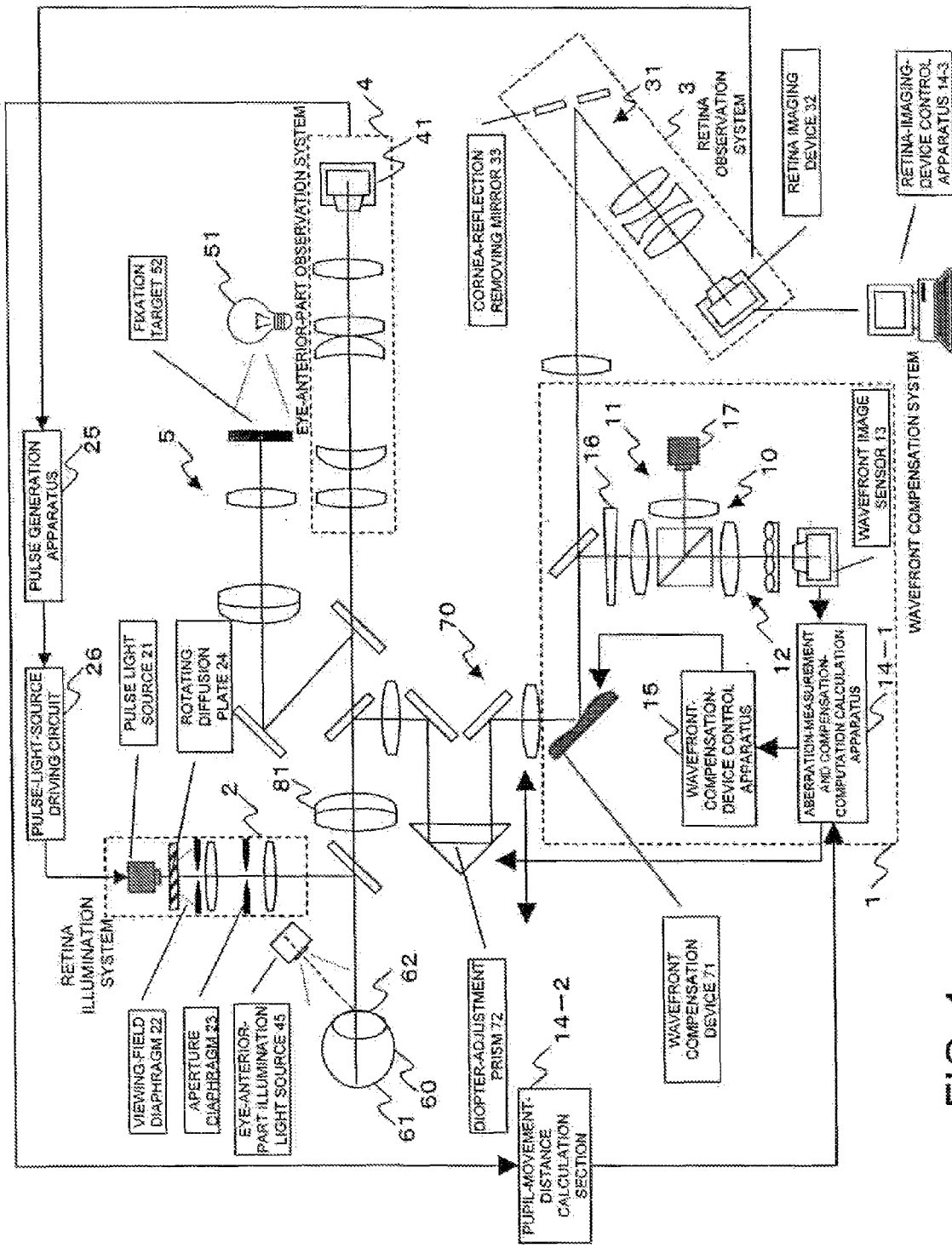
FIG. 1 is a view showing the optical arrangement of a first embodiment.

FIG. 1 is a view showing the optical arrangement of a first embodiment.

A retina observation apparatus (ophthalmologic imaging apparatus) includes a wavefront compensation system 1, a retina illumination system (second illumination optical system) 2, a retina observation system 3, an eye-anterior-part observation system 4, an eye-anterior-part illumination light source 45, a fixation system 5, a compensation optical section 70, a pupil-movement-distance calculation section 14-2, a retina-imaging-device control apparatus (retina-image generation section) 14-3, a pulse generation apparatus 25, and a pulse-light-source driving circuit 26.

The wavefront compensation system (aberration compensation section) 1 includes a first illumination optical system 11, a first light-receiving optical system 12, a wavefront measurement system 10 having a second light-receiving section 13, an aberration-measurement and compensation-computation calculation apparatus (aberration calculation section, hereinafter called a calculation apparatus) 14-1, and a wavefront-compensation-device control apparatus 15. The calculation section 14-1, the pupil-movement-distance calculation section 14-2, and the fundus-image generation section 14-3 can, for example, be provided for one arithmetic section or a plurality of arithmetic sections. In the figure, a retina (eyeground) 61 and a cornea (eye anterior part) 62 are shown in an eye under measurement 60.

The first illumination optical system (point-image projection optical system) 11 includes, for example, a first light source section (for example, a wavefront-measurement light source) 17, and illuminates a minute area (or a target) on the retina of the eye under measurement by a light beam emitted from the first light source section 17. The first illumination optical system 11 also includes, for example, a condenser lens and a relay lens.

It is preferred that the first light source section 17 have high spatial coherence and not-high temporal coherence. As an example, a super luminescence diode (SLD) is employed here as the first light source section 17, and serves as a point light source having high luminance. The first light source section 17 is not limited to an SLD, and may be a laser source, which has high spatial and temporal coherence, if the temporal coherence is appropriately reduced by inserting a rotary diffusing plate. The first light source section 17 may be an LED, which has not-high spatial and temporal coherence, if its quantity of light is sufficient and a pinhole is inserted on the optical path at the position of the light source. The first wavelength of the first light source section 17 used for illumination is, for example, a wavelength in an infrared region, such as 860 nm or 780 nm.

The first light-receiving optical system (point image light-receiving optical system) 12 receives light reflected by and returned from the retina and guides it to the first light-receiving section (such as a wavefront image sensor) 13. The first light-receiving optical system includes a relay lens, a beam splitter, and a conversion member (a splitting device such as a Hartman plate) for converting the reflected light beam into at least 17 beams. The beam splitter is formed of a mirror (such as a polarization beam splitter) which reflects light emitted from the first light source section 17 and transmits the reflected light beam reflected by the retina of the eye under measurement 60 and returned through an afocal lens 81. The conversion member is a wavefront conversion member for converting the reflected light beam into a plurality of beams. A plurality of micro Fresnel lenses disposed on a plane perpendicular to the optical axis can be used as the conversion member. The light beam reflected from the retina 61 is condensed on the first light-receiving section 13 through the conversion member.

The first light-receiving section 13 receives light from the first light-receiving optical system 12, which is transmitted through the conversion member, and generates a first signal.

While the first illumination optical system 11 and the first light-receiving optical system 12 keep a relationship such that, assuming that light emitted from the first light source section 17 is reflected at a point where the light is condensed, the first light-receiving section 13 has the maximum signal peak of the reflected light, a prism 72 can be moved in a direction in which the signal peak obtained by the first light-receiving section 13 increases and stopped at a position where the signal peak reaches the maximum. As a result, the light emitted from the first light-source section 17 is condensed on the eye under measurement.

The second illumination optical system 2 includes, for example, a second light source section (pulse light source or laser light source) 21, a viewing-field diaphragm 22, an aperture diaphragm 23, a rotating diffusion plate 24, a condenser lens, and a beam splitter, and illuminates a predetermined region on the retina (eyeground) of an eye under measurement with a second light beam coming from the second light source section 21.

The second light source section 21 can be a laser diode having a second wavelength (such as 635 nm) or an infrared titanium sapphire laser, for instance. The pulse width preferably falls in a range of several picoseconds to several hundreds of microseconds. When the frame rate of the imaging device is low (about 10 Hz), it is preferable that short pulses are output during data transfer in order to prevent photosensitive epilepsy. The wavelengths can be appropriately selected: for instance, the first light source section 17 for Hartmann measurement has a wavelength of 840 nm, and the eye-anterior-part illumination light source 45 has wavelengths of 850 to 930 nm (860 to 880 nm at present) in the infrared or near-infrared region. The beam splitter can, for example, be a beam splitter that reflects a light beam coming from the second light source section 21 and passes a light beam reflected back from the eye under measurement 60.

As shown in FIG. 1, light is incident from the inside of the pupil and a plate (such as a mirror with an opening used in the figure) which blocks light is inserted at a conjugate point with the cornea and the crystalline lens, so that noise (uninvited reflection) caused by the cornea and others can be removed. The aperture diaphragm 23 of the second illuminating optical system 2 can be disposed close to a conjugate point with the pupil to make an optical system which removes noise light by a cornea-reflection removing mirror, described later. The viewing-field diaphragm 22 is disposed at a conjugate point with the retina. With this, light can be concentrated on an area where a cell is observed, and a load imposed on the person under measurement can be reduced.

When a mirror with an opening is used, the mirror with the opening and the pupil are made to have a conjugate relationship or in the vicinity in order to prevent reflection at a vertex of the cornea. A ring-shaped aperture may also be used when the center thereof has a transmittance of 100%, surroundings of the center have a transmittance of about 10%, and light transmitting the surroundings illuminates the whole of the retina 61.

The rotating diffusion plate 24 reduces speckles of the pulse laser when being rotated at high speed. Although it depends on the exposure period, it is preferable that the plate is rotated at a rotation speed of about 10,000 rpm or more. The pulse generation apparatus 25 generates pulses in synchronization with an exposure signal sent from a retina image sensor 32. When a very fast pulse laser is used such as a picosecond laser, pulses are generated during exposure. The pulse generation apparatus 25 sends the generated signal (pulses) to the pulse-light-source driving circuit 26. The pulse-light-source driving circuit 26 drives the second light source section 21 according to the signal input from the pulse generation apparatus 25 to emit light according to the pulses.

The retina observation system 3 includes a second light-receiving optical system 31 and a second light-receiving section (such as retina imaging device, an fundus-image sensor) 32. The second light-receiving optical system (fundus-image-generation optical system) 31 includes, for example, the afocal lens 81, a beam splitter, a condenser lens, and a cornea-reflection removing mirror 33, and guides light having a second wavelength reflected from the retina 61 to the second light-receiving section 32 through the compensation optical section 70. The beam splitter is formed, for example, of a dichroic mirror which reflects light having the first wavelength and transmits light having the second wavelength. The second light-receiving section 32 receives an fundus-image generated by the second light-receiving optical system 31 and generates a second signal. The second light-receiving section 32 can be formed of a light-receiving device sensitive to the second wavelength (red light).

The cornea-reflection removing mirror 33 is preferably used at a small angle in order to make the pupil conjugate. Using an optical system like a second retina observation system, described later, is an effective way. In the present embodiment, the afocal lens 81, the beam splitter, and others are provided for the second light-receiving optical system 31 for convenience. They may be provided for the first light-receiving optical system 12.

The compensation optical section (aberration compensation section) 70 has a wavefront compensation device 71 such as adaptive optical system (adaptive optics) for compensating measurement light for aberration, the moving prism (diopter-adjustment prism) 72 for moving along the optical axis to compensate a spherical component and/or a spherical lens.

The compensation optical section 70 is disposed in the first and second light-receiving optical systems 12 and 31, and compensates, for example, for the aberration of a reflected light beam reflected by and returned from the eye under measurement 60. The compensation optical section 70 may compensate light emitted from the first light source 17 for aberration to illuminate a minute area on the retina of the eye under measurement by a light beam of which aberration has been compensated for.

The wavefront compensation device 71 can be a variable-shape mirror (a deformable mirror or a variable mirror) or a spatial light modulator such as liquid crystal. An appropriate optical system capable of compensating measurement light for aberration may also be used. A variable-shape mirror changes the reflection direction of light by deforming the mirror by an actuator provided inside the mirror. Other appropriate deforming methods can be used such as a deforming method using a capacitor or a piezoelectric device. A liquid-crystal spatial light modulator uses a liquid-crystal alignment characteristic to modulate a phase, and is used in reflection in many cases in the same way as the variable-shape mirror. When the liquid-crystal spatial light modulator is used, a polarizer is required in an optical path in some cases. The wavefront compensation device 71 may be a transmission-type optical system, in addition to a reflection-type optical system. The wavefront compensation device 71 compensates for aberration by, for example, being deformed according to the output of the wavefront-compensation-device control apparatus 15.

It is preferred that a parallel light beam be incident on the wavefront compensation device 71. Incident light is not limited to parallel light beams. When the eye under measurement 60 has no aberration, for example, light reflected from the retina of the eye under measurement 60 is incident on the wavefront compensation device 71 as a parallel light beam. Light emitted from the first light source section 17 is incident on the wavefront compensation device 71 as a parallel light beam.

The moving prism 72 is moved according to the output of the calculation apparatus 14-1. The moving prism 72 is driven, for example, by an appropriate driving section. A spherical component can be compensated for because the moving prism 72 is moved. The spherical component can be compensated for if a spherical lens is used, instead of moving the moving prism 72.

A motored stage that moves the wavefront compensation device 71 according to the output of a motor control circuit by following the pupil movement distance obtained by the pupil-movement-distance calculation section 14-2 can be further provided. For example, the motored stage moves the wavefront compensation device 71 in a direction traversing the optical axis or in a plane perpendicular to the normal line. With this, a point (such as the center) of the wavefront compensation device 71 always becomes conjugate with a point (such as the pupil center) of the pupil, allowing stable wavefront compensation.

The eye-anterior-part illumination light source 45 illuminates an eye anterior part of the eye under measurement 60. For example, a Placido's ring or a keratoring may be used to project a predetermined pattern on the eye anterior part. When a keratoring is used, a pattern just around the center of curvature of the cornea is obtained by a keratoimage. The wavelength of light emitted from the eye-anterior-part illumination light source 45 is, for example, different from the first wavelength (860 nm or 780 nm in this case), and can be a long wavelength (such as 940 nm).

The eye-anterior-part observation system 4 includes a condenser lens and an eye-anterior-part image sensor 41, and guides a light beam emitted from the eye-anterior-part illumination light source 45 and reflected by and returned from the cornea 62 of the eye under measurement 60, to the eye-anterior-part image sensor 41. As a light source section, an appropriate light source for illuminating the eye under measurement 60 may be used instead of the eye-anterior-part illumination light source 45. The eye-anterior-part observation system 4 can also guide a light beam reflected by and returned from the eye anterior part or the cornea 62 of the eye under measurement 60 when an appropriate pattern (such as a Placido's ring) is projected on the eye under measurement 60, to the eye-anterior-part image sensor 41. The eye-anterior-part image sensor 41 can obtain an eye-anterior-part image. The eye-anterior-part observation system 4 can also be used for alignment. The wavelength of light used for alignment can be a long wavelength (such as 940 nm) different, for example, from the first wavelength (780 nm in this case).

The third illumination optical system (fixation system) 5 includes, for example, an optical path for projecting an eyesight-target for making the eye under measurement 60 have fixation or clouding and fogging, and is provided with a third light source section (such as a lamp) 51, a fixation target 52, and a relay lens. The system 5 can project the fixation target 52 on the retina 61 with a light beam emitted from the third light source section 51, and makes the eye under measurement 60 observe its image.

The wavefront-compensation-device control apparatus 15 deforms the wavefront compensation device 71 according to the output of the calculation apparatus 14-1. For example, the wavefront-compensation-device control apparatus 15 generates a control signal (such as a voltage) for deforming each element of the wavefront compensation device 71, based on wavefront aberration measured by the calculation apparatus 14-1 or based on compensation obtained by the calculation apparatus 14-1, and outputs the generated control signal to the wavefront compensation device 71 to compensate the wavefront.

The calculation apparatus 14-1 obtains optical characteristics that includes higher-order aberrations, of the eye under measurement 60 or of a light beam which was reflected by the eye under measurement 60 and of which aberrations have been compensated for by the compensation optical section 70, according to the output from the first light-receiving section 13. The calculation apparatus 14-1 may receive, instead of the output from the first light-receiving section 13, wavefront measurement data that indicates at least the wavefront aberration of the eye under measurement 60 to obtain the optical characteristics. The calculation apparatus 14-1 also determines the amount of compensation for the wavefront compensation device according to the obtained optical characteristics and outputs the amount of compensation to the wavefront-compensation-device control apparatus 15.

The pupil-movement-distance calculation section 14-2 measures the displacement of the eye under measurement (such as the movement distance of the pupil) from the eye-anterior-part image generated by the eye-anterior-part image sensor 41. The pupil-movement-distance calculation section 14-2 can measure the movement distance of the center of the pupil as the displacement of the eye under measurement, but it may also obtain the movement distance of an appropriate position of the eye under measurement, such as the vertex of the cornea. The fundus-image generation section 14-3 obtains an fundus-image generated by the second light-receiving section 32, and displays or outputs the fundus-image.

Conjugate Relationship

The retina 61 of the eye under measurement 60, the fixation target 52 in the fixation system 5, the first light source section 17, and the first light-receiving section 13 are conjugate. The pupil (iris) of the eye under measurement 60 and the conversion member (Hartman plate) of the first light-receiving optical system 12 are conjugate. The rotating diffusion plate 24 is conjugate with the pupil (an image is formed on the pupil), and can uniformly illuminate the whole of most of the retina 61.

Alignment Adjustment

Alignment adjustment will next be described. Alignment adjustment can be performed, for example, by the eye-anterior-part observation system 4.

Since an image of the eye under measurement 60 is formed on the eye-anterior-part image sensor 41 by the eye-anterior-part illumination light source 45 (light source section), which illuminates the cornea 62 of the eye under measurement 60, alignment adjustment needs to be performed such that the center of the pupil matches the optical axis by using the image of the eye under measurement 60.

When a light source for illuminating the eye under measurement 60 by parallel light beams through the condenser lens, the beam splitter, and the afocal lens 81 is added to the eye-anterior-part observation system 4, light beams reflected by the cornea 62 of the eye under measurement 60 are returned as if they were diverging from a point positioned at half the radius of curvature of the cornea 62. The diverging light beams pass through the afocal lens 81, the beam splitter, and the condenser lens, and the eye-anterior-part image sensor 41 receives the light beams as a spot image. If the spot image on the eye-anterior-part image sensor 41 is not on the optical axis, the retina observation apparatus is moved up and down and from side to side so that the spot image is on the optical axis. When the spot image is brought onto the optical axis, alignment adjustment is completed.

1.3 Electrical-System Configuration

Figure 2:
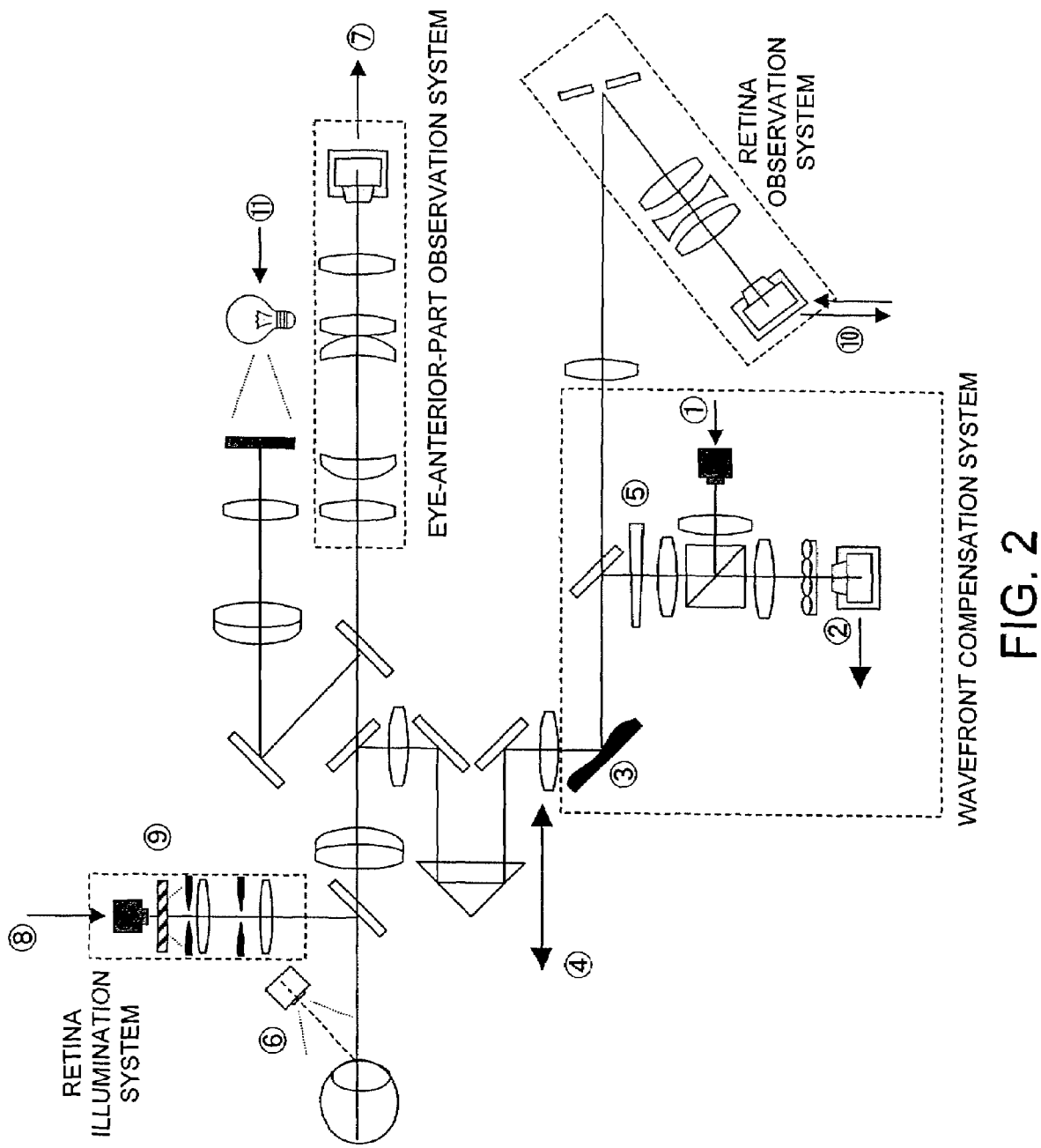
FIG. 2 is a view showing signals in the first embodiment.
Figure 3:
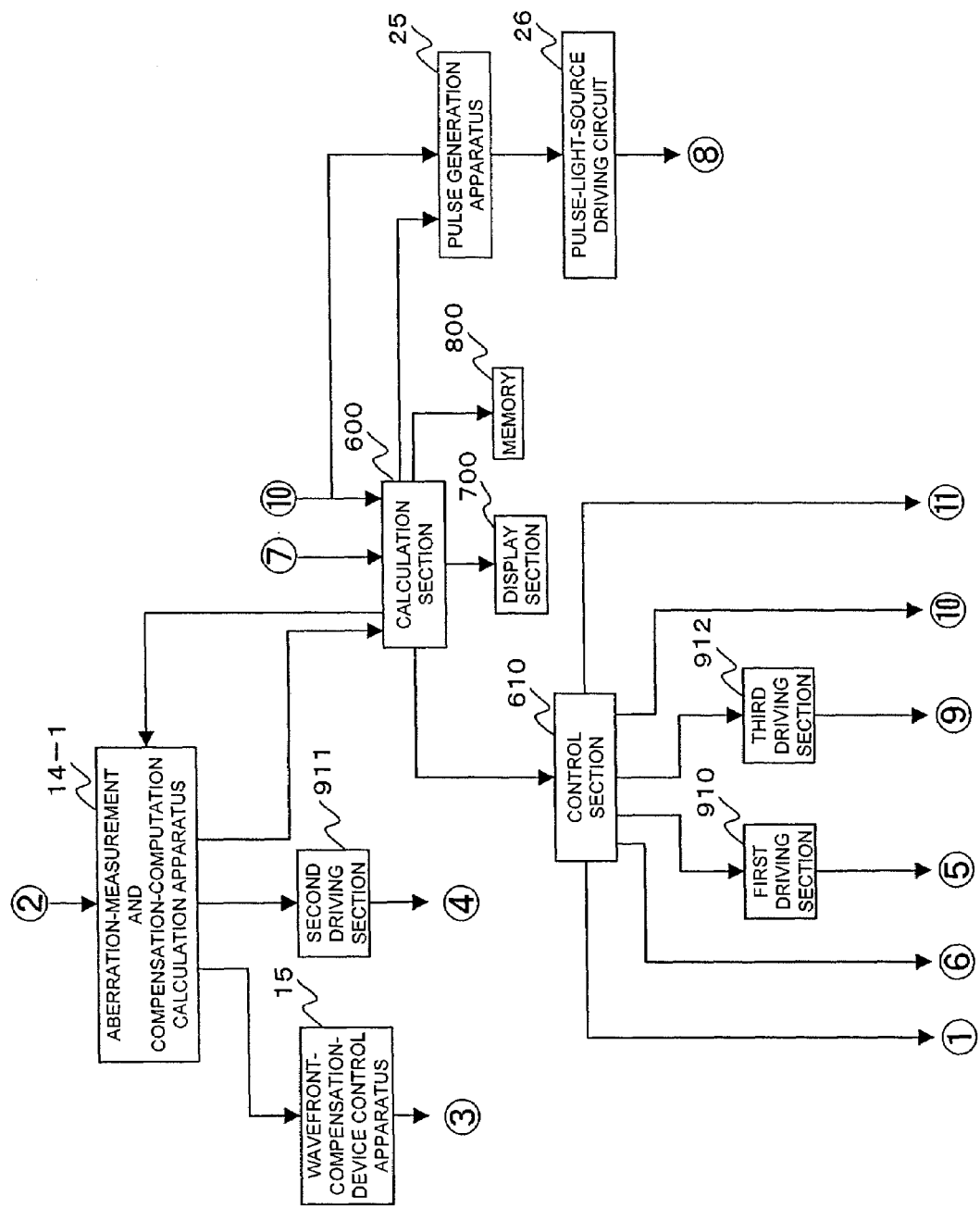
FIG. 3 is a block diagram of an electrical system in the first embodiment.

FIG. 3 is a block diagram of an electrical system of the ophthalmologic imaging apparatus. FIG. 2 is a view showing signals in the first embodiment.

In the structure of the electrical system of the ophthalmologic imaging apparatus, a calculation section 600, a control section 610, a display section 700, a memory 800, a first driving section 910, a second driving section 911, and a third driving section 912 are provided. The ophthalmologic imaging apparatus may further include an input section. As the input section, a pointing device for specifying a button, an icon, a position, an area, and others displayed on the display section 700, or a keyboard for inputting various types of data can be provided.

The calculation section 600 receives a second signal (10) from the second light-receiving section 32, a signal (7) from the eye-anterior-part observation system 4, and a signal from the calculation apparatus 14-1.

For example, the calculation section 600 receives a signal (7) from the eye-anterior-part observation system 4 and performs, for example, alignment adjustment. The calculation section 600 outputs signals corresponding to these processes, or other signals and data to the control section 610, which controls an electrical driving system, the display section 700, the memory 800, the calculation apparatus 14-1, and the pulse generation apparatus 25, if necessary.

The control section 610 controls turning on and off of the first light-source section 17, the third light-source section 51, and the eye-anterior-part illumination light source 45, and controls the first driving section 910 and the third driving section 912 according to control signals sent from the calculation section 600. For example, the control section 610 outputs a signal (1) to the first light-source section 17, a signal (6) to the eye-anterior-part illumination light source 45, a signal (10) to the second light-receiving section 32, a signal (11) to the third light-source section 51, and further signals to the first driving section 910 and the third driving section 912, according to signals corresponding to calculation results in the calculation section 600.

The aberration-measurement and compensation-computation calculation apparatus 14-1 receives a first signal (2) from the first light-receiving section 13. According to the received signal, the calculation apparatus 14-1 calculates optical characteristics of the eye under measurement 60, such as aberrations and the amount of aberrations, and the amount of compensation used by the wavefront compensation device 71 for compensation. The calculation apparatus 14-1 outputs signals corresponding to these calculation results, or other signals and data to the calculation section 600, the wavefront-compensation-device control apparatus 15, and the second driving section 911, if necessary. The calculation apparatus 14-1 may be included in the calculation section 600. A signal may be input to the second driving section 911 through the control section 610.

The wavefront-compensation-device control apparatus 15 outputs a signal (3) according to the signal received from the calculation apparatus 14-1 to control the wavefront compensation device 17 so as to compensate for aberrations.

The pulse generation apparatus 25 receives a signal from the calculation section 600 and the signal (10) from the second light-receiving section 32. The pulse generation apparatus 25 generates pulses according to the received signals. The pulse generation apparatus 25 outputs a signal corresponding to the generated pulses or other signals and data to the pulse-light-source driving circuit 26. According to the signal received from the pulse generation apparatus 25, the pulse-light-source driving circuit 26 outputs a signal (8) to the second light source section 21.

The display section 700 displays an imaging result (a retina image and others). The memory 800 stores measured aberrations, a captured image and time, settings such as a predetermined exposure period "t" and the number of pulses P, and others, if necessary. The calculation section 600 reads data from the memory 800 or writes data into the memory 800, if necessary.

The first driving section 910 outputs a signal (5) at least during the operation of the retina image sensor 32 to rotate a rotary prism 16. The second driving section 911, for example, outputs a signal (4) to drive movement means for the moving prism 72 to move the moving prism 72 along the optical axis. The third driving section 912, for example, outputs a signal (9) to rotate the rotating diffusion plate 24 at high speed.

1.4. Aberration Measurement

Next, an aberration measurement (a Zernike analysis) will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 13 through the conversion member, for example Hartmann plate.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate.

Besides, with respect to the wavefront aberrations W(X, Y), when the horizontal and vertical coordinates of the first light receiving part 13 are denoted by (x, y), a distance between the Hartmann plate and the first light receiving part 13 is denoted by f, and a movement distance of a point image received by the first light receiving part 13 is denoted by (Δx, Δy), the following expression is established.

$$\frac{\partial W(X, Y)}{\partial X} = \frac{\Delta x}{f}$$

$$\frac{\partial W(X, Y)}{\partial Y} = \frac{\Delta y}{f}$$

Where, the Zernike polynomials $Z_i^{2j-i}$ are expressed by the following numerical expressions. (More specifically expressions, for example, see JP-A-2002-209854.)

$$Z_n^m = R_n^m(r) \left\{ \begin{array}{c} \sin \\ \cos \end{array} \right\} \{m\theta\}$$

$$m > 0 \; \sin$$

$$m \leq 0 \; \cos$$

$$R_n^m(r) = \sum_{S=0}^{(n-m)/2} (-1)^S \frac{(n-S)!}{S!\left\{\frac{1}{2}(n-m)-S\right\}! \left\{\frac{1}{2}(n+m)-S\right\}!} r^m$$

Incidentally, with respect to the Zernike coefficients $C_i^{2j-1}$, specific values can be obtained by minimizing the squared error expressed by the following numerical expression.

$$S(x) = \sum_{i=1}^{data\;number} \left[ \left\{\frac{\partial W(X_i, Y_i)}{\partial X} - \frac{\Delta x_i}{f}\right\}^2 + \left\{\frac{\partial W(X_i, Y_i)}{\partial Y} - \frac{\Delta y_i}{f}\right\}^2 \right]$$

Where, W(X, Y): wavefront aberrations, (X, Y): Hartmann plate coordinates, (Δx, Δy): a movement distance of a point image received by the first light receiving part 13, f: a distance between the Hartmann plate and the first light receiving part 13.

The calculation apparatus 14-1 calculates the Zernike coefficients $C_i^{2j-i}$ and uses this to obtain eye optical characteristics such as spherical aberrations, coma aberrations, and astigmatism aberrations. The calculation apparatus 14-1 calculates aberration quantities $RMS_i^{2j-i}$ using the Zernike coefficients $C_i^{2j-i}$ by the following numerical expression.

$$RMS_i^{2j-i} = \sqrt{\frac{\varepsilon_i^{2j-i}}{2(i+1)}} \, c_i^{2j-i}$$

-continued $$(\varepsilon_i^{2j-i} = 2(2j = i), \varepsilon_i^{2j-i} = 1(2j \neq i))$$

1.5 Operation

Figure 4:
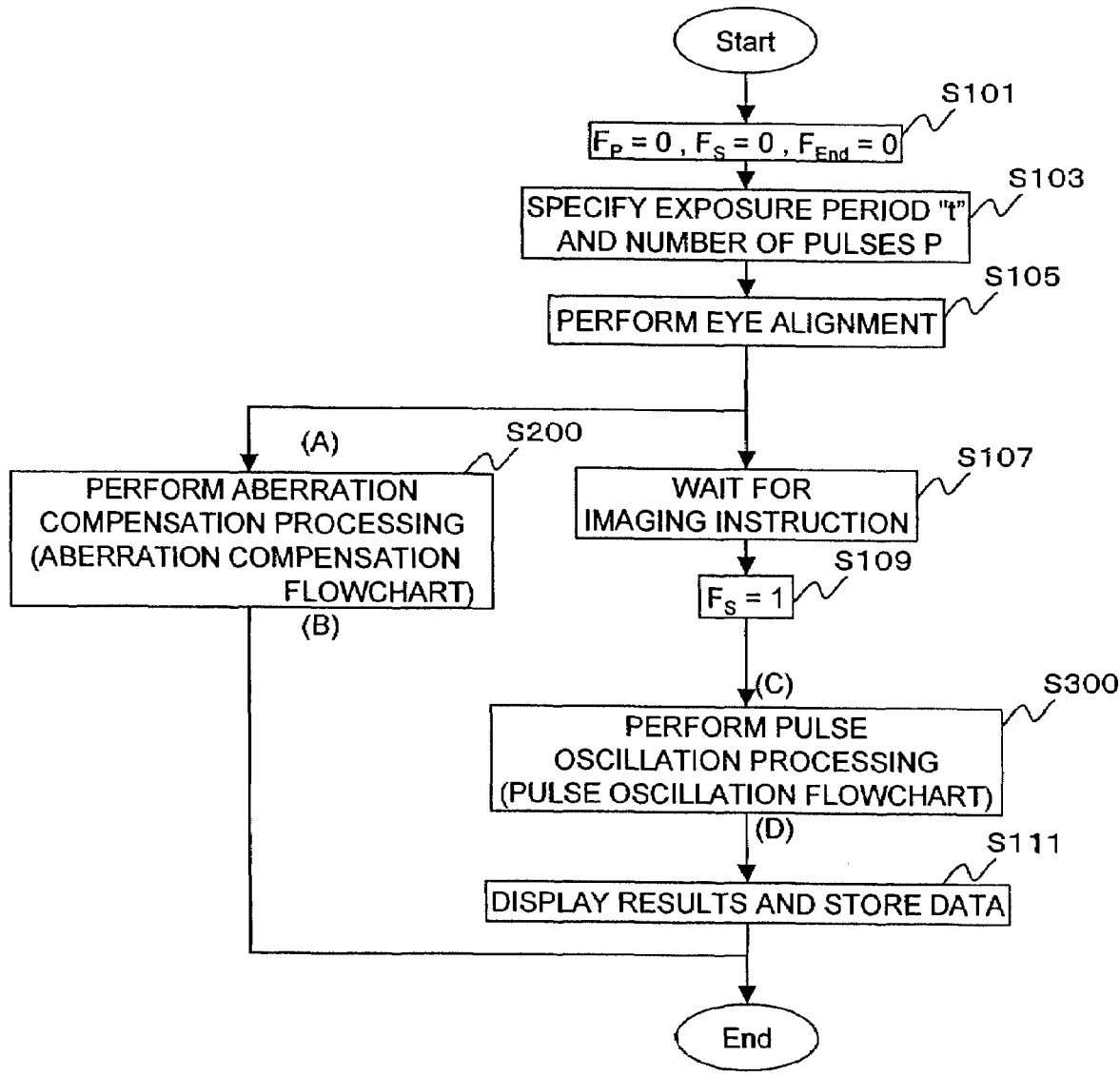
FIG. 4 is an overall flowchart in the first embodiment.

FIG. 4 is an overall flowchart in the first embodiment.

The calculation section 600 first specifies initial settings in step S101. For example, the calculation section 600 sets a flag $F_P$ to zero, a flag $F_S$ to zero, and a flag $F_{End}$ to zero. The flag $F_S$ in the present embodiment is, for example, used to determine whether imaging has been specified or not. When it is set to "1", it means that imaging has been specified; and when it is set to "0", it means that imaging has not been specified. The flag $F_P$ is, for example, used to determine whether the amount of aberrations is smaller than a threshold determined in advance. When it is set to "1", it means that the amount of aberrations is smaller than the threshold; and when it is set to "0", it means that the amount of aberrations is not smaller than the threshold. The flag $F_{End}$ is used to determine whether imaging is to be finished. When it is set to "1", it means that imaging is to be finished; and when it is set to "0", it means that imaging is not to be finished. These flags may be used for other purposes, if necessary.

Next, the calculation section 600 specifies the exposure period "t" and the number of pulses P in step S103. The exposure period "t" and the number of pulses P may be input from an appropriate input apparatus, or values thereof stored in advance in the memory 800 may be read. The calculation section 600 performs alignment of the eye under measurement in step S105. Another light source may be used to generate an alignment spot for eye alignment. In the present embodiment, for example, a light beam is projected to the eye anterior part, a light beam reflected from the eye anterior part is incident on the eye-anterior-part image sensor 41, and the operator moves the whole apparatus or the eye under measurement such that the center of the eye anterior part matches the origin of the eye-anterior-part image sensor 41 to perform eye alignment. Eye alignment may be performed at any appropriate timing.

Then, the calculation apparatus 14-1 performs aberration compensation processing for the eye under measurement in step S200. Details of the aberration compensation processing will be described later with reference to an aberration compensation flowchart. The calculation section 600 performs the following processes in parallel to step S200.

The calculation section 600 waits for an imaging instruction in step S107. For example, the operator may input an imaging instruction at the input section, or the calculation section 600 or other sections may automatically determine an imaging start. Alternatively, the display section 700 may display a message prompting an input of an imaging start instruction. When the calculation section 600 receives an imaging instruction, the calculation section 600 sets, for example, the flag $F_S$ to "1" in step S109.

Then, the calculation section 600 performs pulse oscillation processing in step S300. Details of the pulse oscillation processing will be described later with reference to a pulse oscillation flowchart. Then, the calculation section 600 displays data that includes a plurality of retina images obtained in the pulse oscillation processing, on the display section 700 in step S111. The calculation section 600 may store necessary data in the memory 800.

Figure 5:
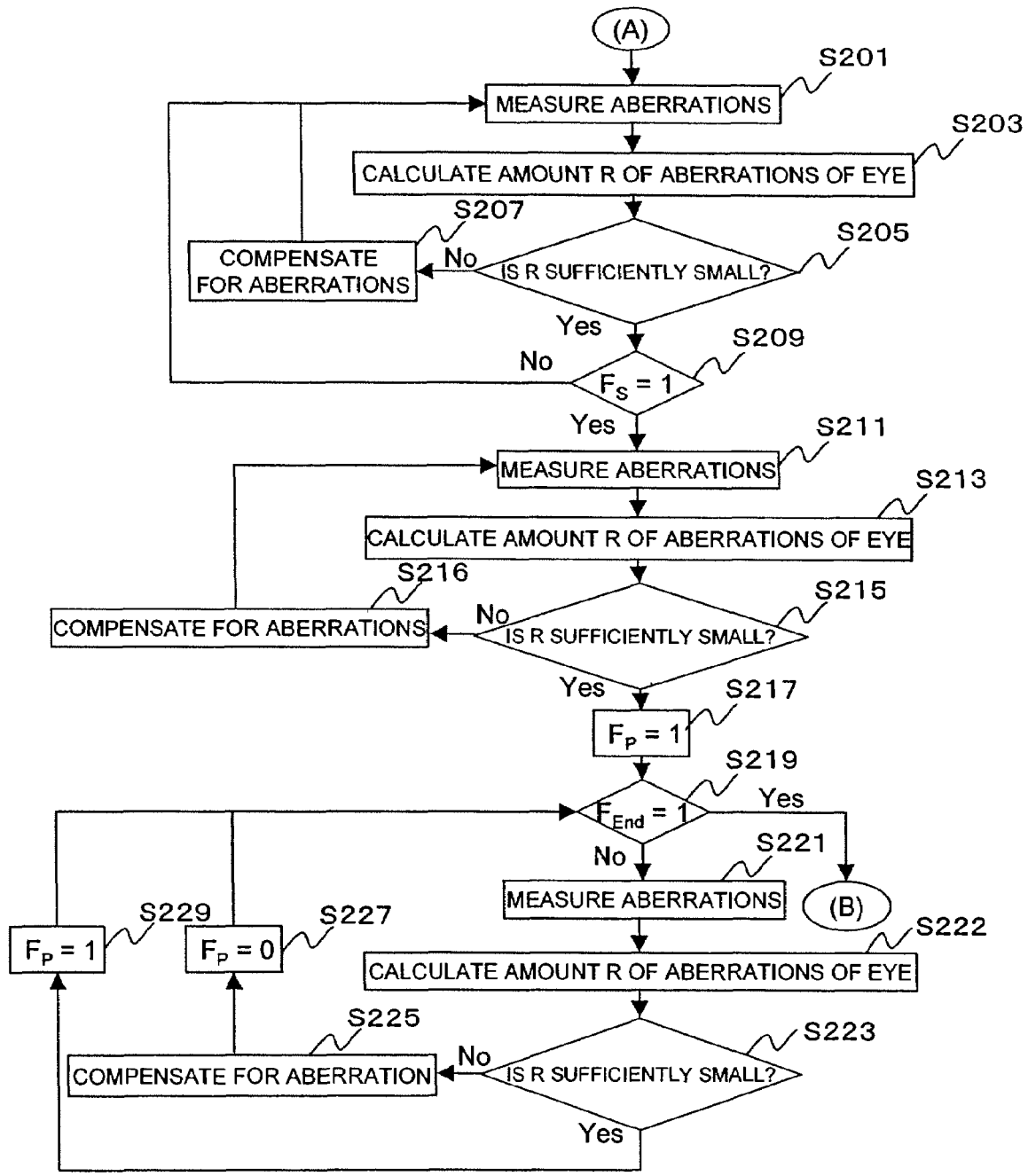
FIG. 5 is a flowchart of aberration compensation.

FIG. 5 is the aberration compensation flowchart, which is a detailed flowchart of step S200, described above.

The calculation apparatus 14-1 first measure the aberrations of the eye under measurement (eye) in step S201. Then, the calculation apparatus 14-1 calculates the amount R of the aberrations of the eye in step S203. For example, the calculation apparatus 14-1 calculates the amount R of aberrations of the eye according to the measurement results (Zernike coefficients $c_i^{2j-1}$, for example) of the aberration measurement obtained in step S201 and stores the calculation result in the memory 800. The amount R of aberrations can be calculated as the standard deviation of the measurement results from an ideal wavefront (aplanatic state). For example, the amount R of aberrations can be obtained in a simplified manner by the use of the Zernike coefficients by the following expression. In the expression, "order" means the order of the Zernike coefficients, and "order" is, for example, set to a value such as 4 or 6.

$$R = \sqrt{\sum_{i=0}^{order} \sum_{j=0}^{i} \frac{\varepsilon_i^{2j-i}}{2(i+1)} (c_i^{2j-i})^2}$$

$$(\varepsilon_i^{2j-i} = 2(2j = i), \varepsilon_i^{2j-i} = 1(2j \neq i))$$

Next, the calculation apparatus 14-1 determines in step S205 whether the amount R of aberrations is sufficiently small or not. For example, the calculation apparatus 14-1 determines whether the amount R of aberrations is smaller than a threshold determined in advance. If the amount R of aberrations is not sufficiently small in step S205, the calculation apparatus 14-1 performs an aberration compensation process in step S207. For example, the calculation apparatus 14-1 moves the moving prism 72 through the second driving section 911 and controls the wavefront compensation device 71 through the wavefront-compensation-device control apparatus 15 to compensate for the aberrations so as to cancel out the measured aberrations. Then, the processing returns to step S201. When the amount R of aberrations is sufficiently small in step S205, the calculation apparatus 14-1 determines in step S209 whether an imaging instruction has been received (in the current case, whether the flag $F_S$ has been set to "1"). If an imaging instruction has not been received in step S209, the processing returns to step S201.

When an imaging instruction has been received in step S209, the calculation apparatus 14-1 executes processes in step S211 to step S216. Since the processes in step S211 to step S216 are the same as those in step S201 to step S207, a description thereof will be omitted here. The processes in step S211 to step S216 may be omitted.

When the amount R of aberrations is sufficiently small in step S215, the calculation apparatus 14-1 sets the flag $F_P$ to "1" in step S217. When the flag $F_P$ is set to "1", pulse oscillation and an exposure of the imaging device (CCD) 32 start, as described later.

Then, the calculation apparatus 14-1 determines in step S219 whether the flag $F_{End}$ is "1" or not. When the flag $F_{End}$ is "1", it means, for example, that pulse oscillation has finished. When pulse oscillation has not finished in step S219, the calculation apparatus 14-1 executes processes in step S221 to step S225. Since the processes in step S221 to step S225 are the same as those in step S201 to step S207, a description thereof will be omitted here. The processes in step S221 to step S225 are executed in parallel to pulse oscillation.

After the process in step S225, the calculation apparatus 14-1 sets the flag $F_P$, for example, to "0" in step S227, and the processing returns to step S219. When the amount R of aberrations is sufficiently small in step S223, the calculation apparatus 14-1 sets the flag $F_P$, for example, to "1" in step S229, and the processing returns to step S219.

In this way, the calculation apparatus 14-1 repeats the processes in step S219 to step S229. When it is determined in step S219 that the flag $F_{End}$ is "1", the aberration compensation processing is terminated (go to (B) in FIG. 5).

Figure 6:
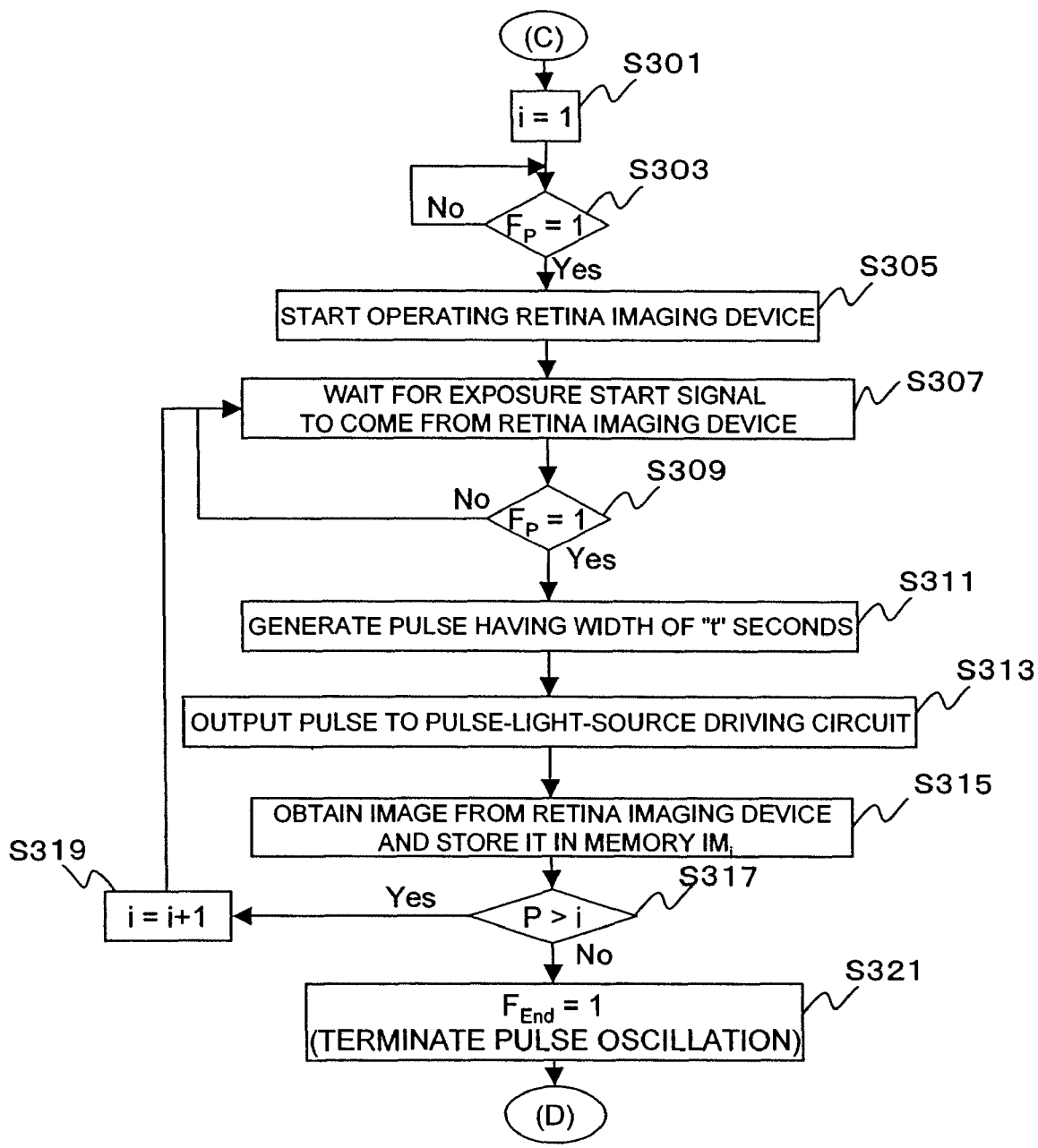
FIG. 6 is a flowchart of pulse oscillation.

FIG. 6 is the pulse oscillation flowchart, which is a detailed flowchart of step S300, described above.

The calculation section 600 first specifies an initial setting in step S301. For example, the calculation section 600 sets a parameter "i" to "1". The parameter "i" indicates, for example, the number of pulse oscillation operations or the number of imaging operations. Next, the calculation section 600 determines in step S303 whether the flag $F_P$ is "1" or not. If the flag $F_P$ is not "1", the calculation section 600 repeats the process in step S303. When the flag $F_P$ is "1" (that is, when the amount of aberrations is small), the calculation section 600 starts the operation of the retina imaging device 32 through the control section 610 in step S305. The calculation section 600 waits for an exposure start signal output from the retina imaging device 32 to come, in step S307.

The retina imaging device 32 starts operation due to the process in step S305 and outputs an exposure start signal at the timing when exposure starts. For example, the retina imaging device 32 stops exposure when "t" seconds have elapsed after the start of the exposure and outputs an image obtained. After outputting the image, the retina imaging device 32 again starts exposure and outputs an exposure start signal. The retina imaging device 32 repeats these operations.

Next, when the calculation section 600 receives an exposure start signal from the retina imaging device 32, the calculation section 600 determines in step S309 whether the flag $F_P$ is "1" or not. The process in step S309 may be omitted. If the flag $F_P$ is not "1" in step S309, the processing returns to step S307, and the calculation section 600 waits for the next exposure start signal to come. When the flag $F_P$ is "1" in step S309, the pulse generation apparatus 25 generates a pulse having a width of "t" seconds, which is the exposure period specified in advance, in step S311. The pulse may have a width shorter than the exposure period, "t" seconds. Then, the pulse generation apparatus 25 outputs the generated pulse to the pulse-light-source driving circuit 26 in step S313. The pulse light source 21 emits pulse light corresponding to the pulse generated in step S311, under the control of the pulse-light-source driving circuit 26.

When exposure for "t" seconds, which is the predetermined exposure period, finishes, the calculation section 600 reads data such as an image from the retina imaging device 32 and stores it in the memory 800 as data $IM_i$ corresponding to the parameter "i" in step S315. The time and other items may be further stored. Then, the control section 600 determines in step S317 whether the parameter "i" is smaller than P, that is, whether pulse oscillation has been performed P times. When the parameter "i" is smaller than P in step S317, the calculation section 600 increments "i" (for example, i=i+1) in step S319, and the processing returns to step S307.

In this way, the calculation section 600 repeats the processes in step S307 to step S319. When the predetermined number P of pulses have been generated, it is determined in step S317 that the parameter "i" is not smaller than P. The calculation section 600 sets the flag $F_{End}$ to "1" in step S321 and terminates the pulse oscillation processing (go to (D) in FIG. 6). As described above, when the flag $F_{End}$ is set to "1", the aberration compensation processing is terminated.

FIG. 7 is a view showing obtained retina images.

FIG. 7(a) shows a retina image obtained by usual imaging without using adaptive optics, which makes detailed observation difficult due to the aberrations of the eye. FIG. 7(b) shows a retina image obtained by a conventional adaptive optics. In that case, it is difficult to observe an object that is moving. FIG. 7(c) shows a plurality of retina images obtained by an apparatus that includes adaptive optics, a pulse light source, and a shutter synchronization mechanism, as in the present embodiment. A moving object can also be observed consecutively in detail. In addition, since light necessary for obtaining a retina image is incident on the eye under measurement 60 only for CCD exposure periods with the use of pulse light beams, a small load is imposed on the eye under measurement 60 and observation can be possible for a long period of time. The images shown in FIG. 7(c) also serve as display examples on the display section 700.

Figure 8:
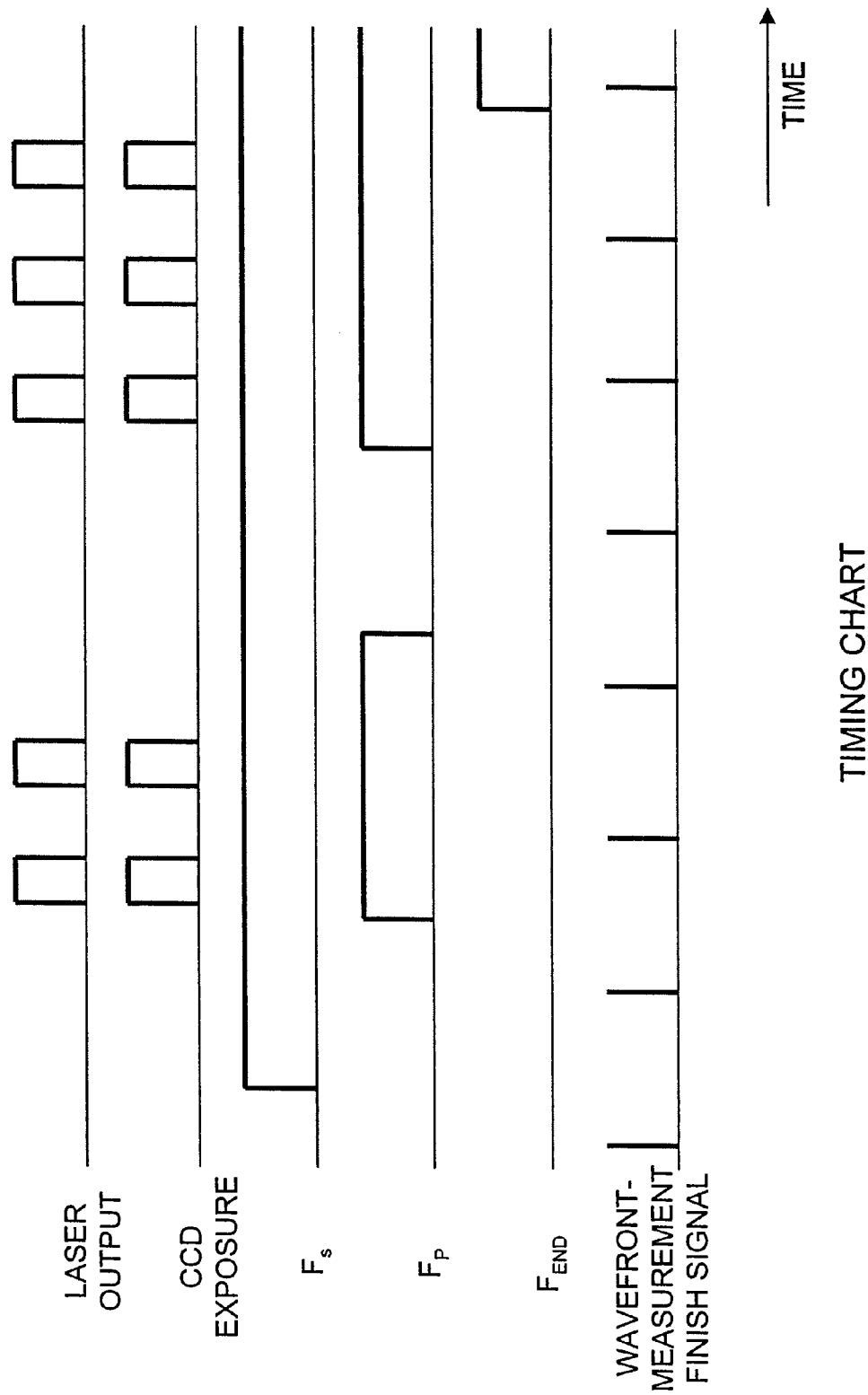
FIG. 8 is a timing chart of signals that allow successful images to be taken.

FIG. 8 is a timing chart for obtaining successful images, as in the present embodiment.

When the flag $F_S$, indicating that an imaging instruction has been received, and the flag $F_P$, indicating that the aberrations have become small due to aberration compensation, are both set (are both "1"), the pulse light source 21 outputs a pulse in synchronization with the exposure of the retina imaging device (CCD) 32. Aberration compensation is performed in parallel to pulse oscillation and retina-image acquisition. When the flat Fp becomes "0" (the aberrations become large) at the middle, the output from the laser light source 21 is stopped. In that case, control may be performed such that the retina imaging device (CCD) 32 is not exposed to light, or such that exposure is performed but data is not obtained or stored.

Eye aberrations change, for example, due to eye movement, a temporal change in tears on the cornea, adjustment of the crystalline lens made to look in the vicinity or in the distance, and other factors. After the measured amount of aberrations becomes smaller than a threshold due to aberration compensation, the amount of aberrations may again become larger than the threshold. This amount of aberrations, if any, is compensated for by wavefront compensation processing executed in parallel. When the flag $F_P$ is again set to "1", the pulse light source 21 outputs a pulse in synchronization with the exposure of the retina imaging device (CCD) 32. In this way, the pulse is output the specified P times (five times in the case shown in the figure), allowing a plurality of retina images to be taken. When the pulse has been output P times, the flag $F_{End}$, used to terminate imaging, is set and imaging is finished.

Figure 9:
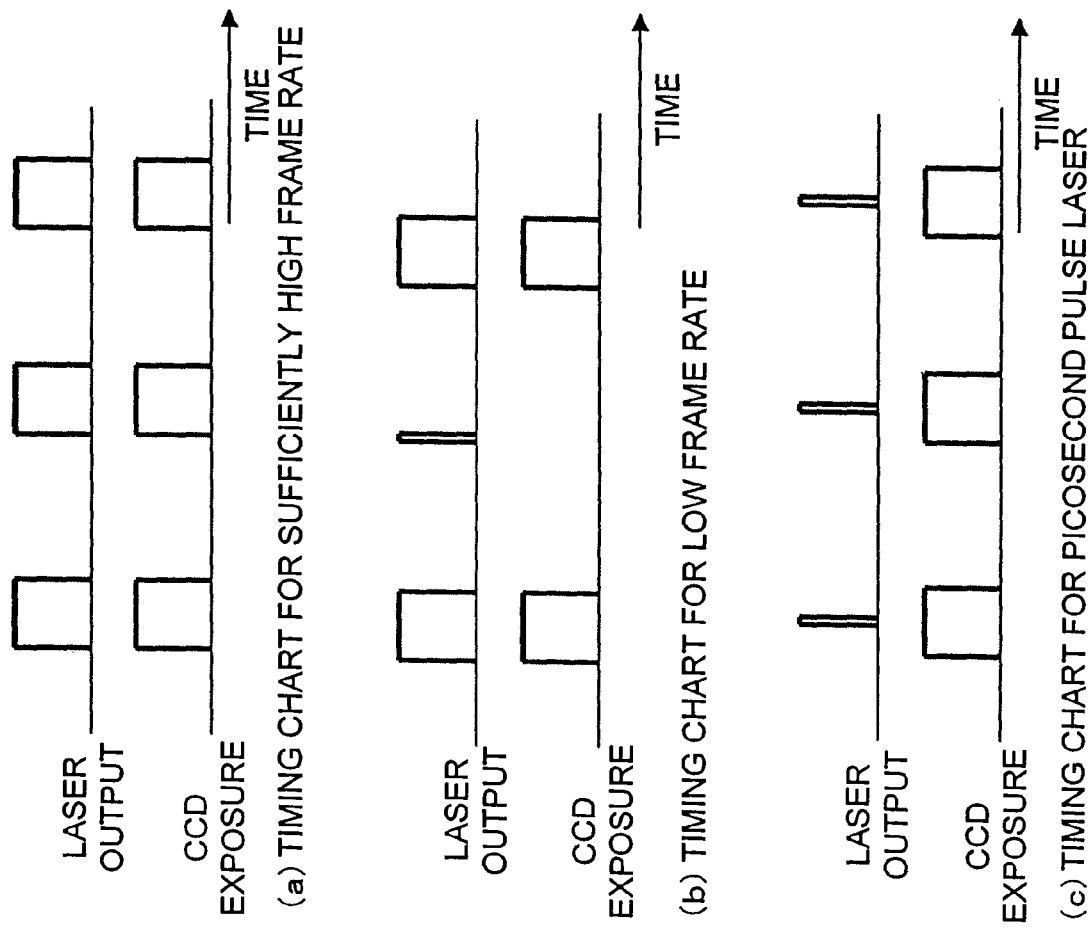
FIG. 9 shows timing charts in the first embodiment.

FIG. 9 is a timing chart showing laser outputs and CCD exposures. FIG. 9(a) shows a timing chart for a case in which the frame rate is sufficiently high. When the frame rate is high, CCD exposures and laser outputs are synchronized, for example. FIG. 9(b) shows a timing chart for a case in which the frame rate is low. When the frame interval is more than a threshold, a short pulse may be output between laser outputs synchronized with CCD exposures. FIG. 9(c) shows a timing chart for a picosecond pulse laser. When a picosecond pulse laser is used, each laser output can be positioned within the period of a CCD exposure (near the center thereof, for example).

2. Second Embodiment

2.1 Outline

In a second embodiment, between pulse light beams, a different pulse light beam is mixed (observation light is interrupted) to obtain a high-magnification image and a low-magnification image by one light source and one light-receiving device. The present embodiment facilitates the acquisition of a high-magnification image at a desired portion by obtaining a wide-range (low-magnification) image. In addition, it is made easier to understand the portion where a high-magnification image was captured, in the whole area. Conventionally, in order to obtain a low-magnification image and a high-magnification image at the same time, a separate imaging device and a separate light source are required. Further, an alignment shift is likely to occur. These issues will be solved when a low-magnification image and a high-magnification image can be obtained with a short time difference. In the present embodiment, pulses sent to a pulse light source are modulated and the optical path is changed by optical switches to obtain high-magnification and low-magnification retina images in a compact system.

2.2 Optical Arrangement

Figure 10:
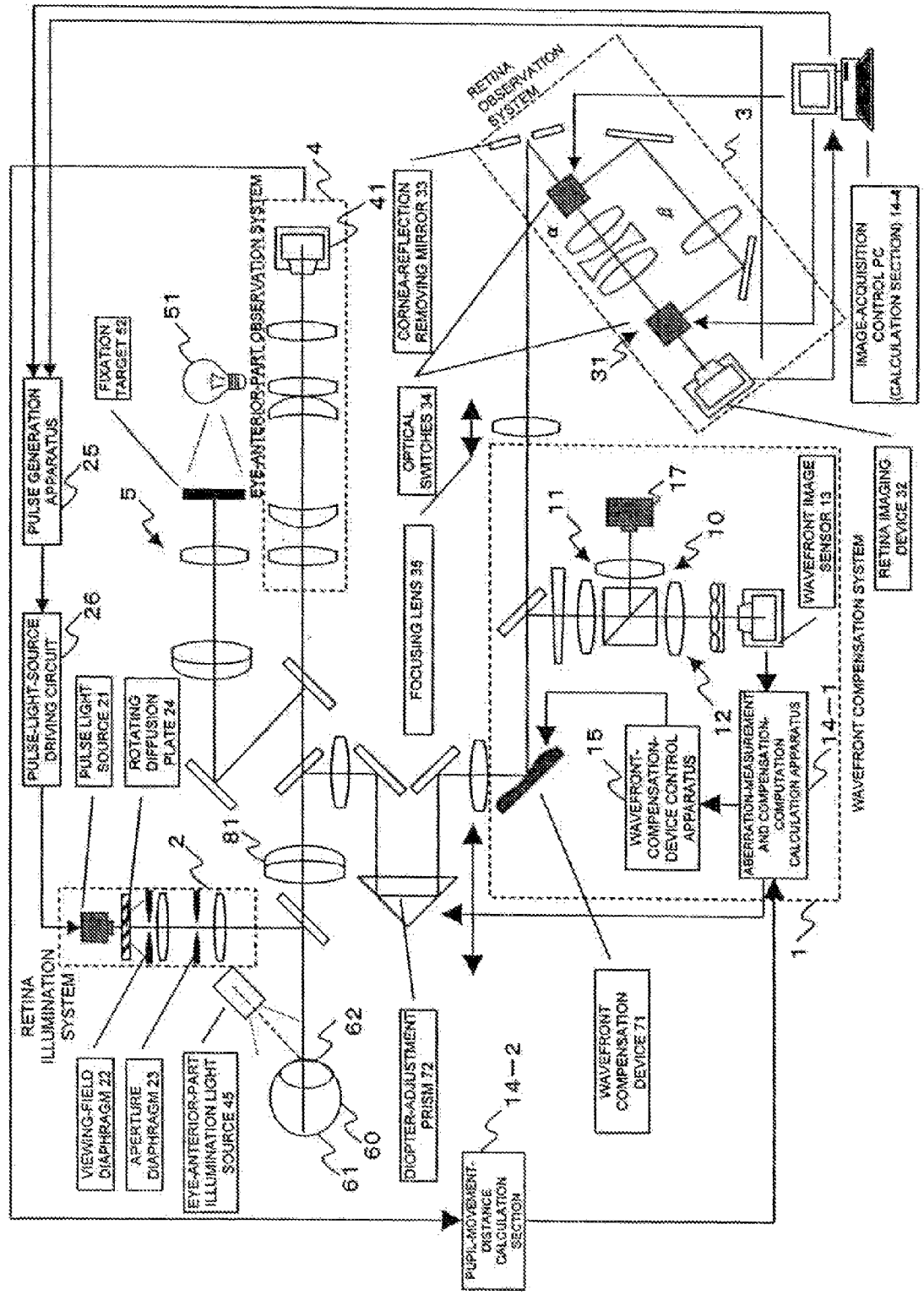
FIG. 10 is a view showing the optical arrangement of a second embodiment.

FIG. 10 is a view showing the optical arrangement of the second embodiment.

A retina observation apparatus includes a wavefront compensation system 1, a retina illumination system 2, a retina observation system 3, an eye-anterior-part observation system 4, an eye-anterior-part illumination light source 45, a fixation system 5, a compensation optical section 70, a pupil-movement-distance calculation section 14-2, an image-acquisition control PC 14-4, a pulse generation apparatus 25, and a pulse-light-source driving circuit 26. The same parts as in the first embodiment are assigned the same symbols as those in the first embodiment, and a description thereof is omitted.

The retina observation system 3 further includes a variable magnification section and a focusing lens 35. The variable magnification section includes, for example, optical switches 34, an optical path a formed of a high-magnification optical system, and an optical path β formed of a low-magnification optical system. The retina observation system 3 can change the optical path when the optical switches 34 are switched by an external unit (for example, by the image-acquisition control PC 14-4). In the present embodiment, the optical path a corresponds to the high-magnification system, and the optical path β corresponds to the low-magnification system. For example, when the optical switches 34 are on, an image is formed on a second light-receiving section (retina imaging device) 32 through the optical path β; and when the optical switches 34 are off, an image is formed on the second light-receiving section (retina imaging device) 32 through the optical path α. To obtain an image of a desired portion at a high magnification, retina alignment is performed, the optical switches 34 are set on to obtain a retina image, and a fixation target 52 is moved (shifted) perpendicularly to the optical axis such that the desired portion comes to the center. In the present embodiment, the image-acquisition control PC (calculation section) 14-4 has the same function as the retina-imaging-device control apparatus (retina-image generation section) 14-3 used in the first embodiment, and further has a function for controlling the optical switches 34 and other functions.

The optical switches 34 preferably operate at a higher rate than the transfer rate of the second light-receiving section (retina imaging device) 32. For example, galvanomirrors or optical switches using the Pockels effect can be used.

2.3 Electrical-System Configuration

Figure 11:
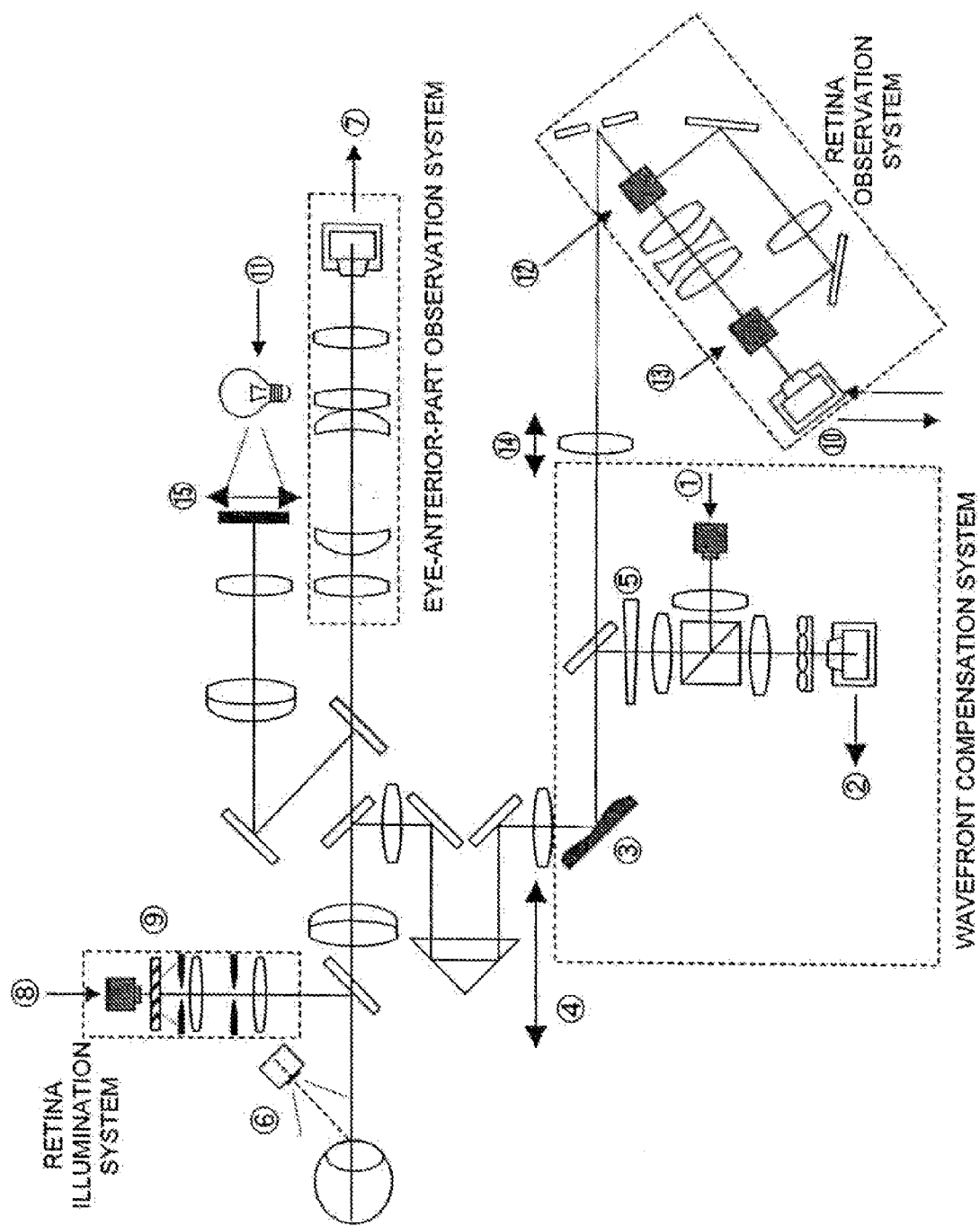
FIG. 11 is a view showing signals in the second embodiment.
Figure 12:
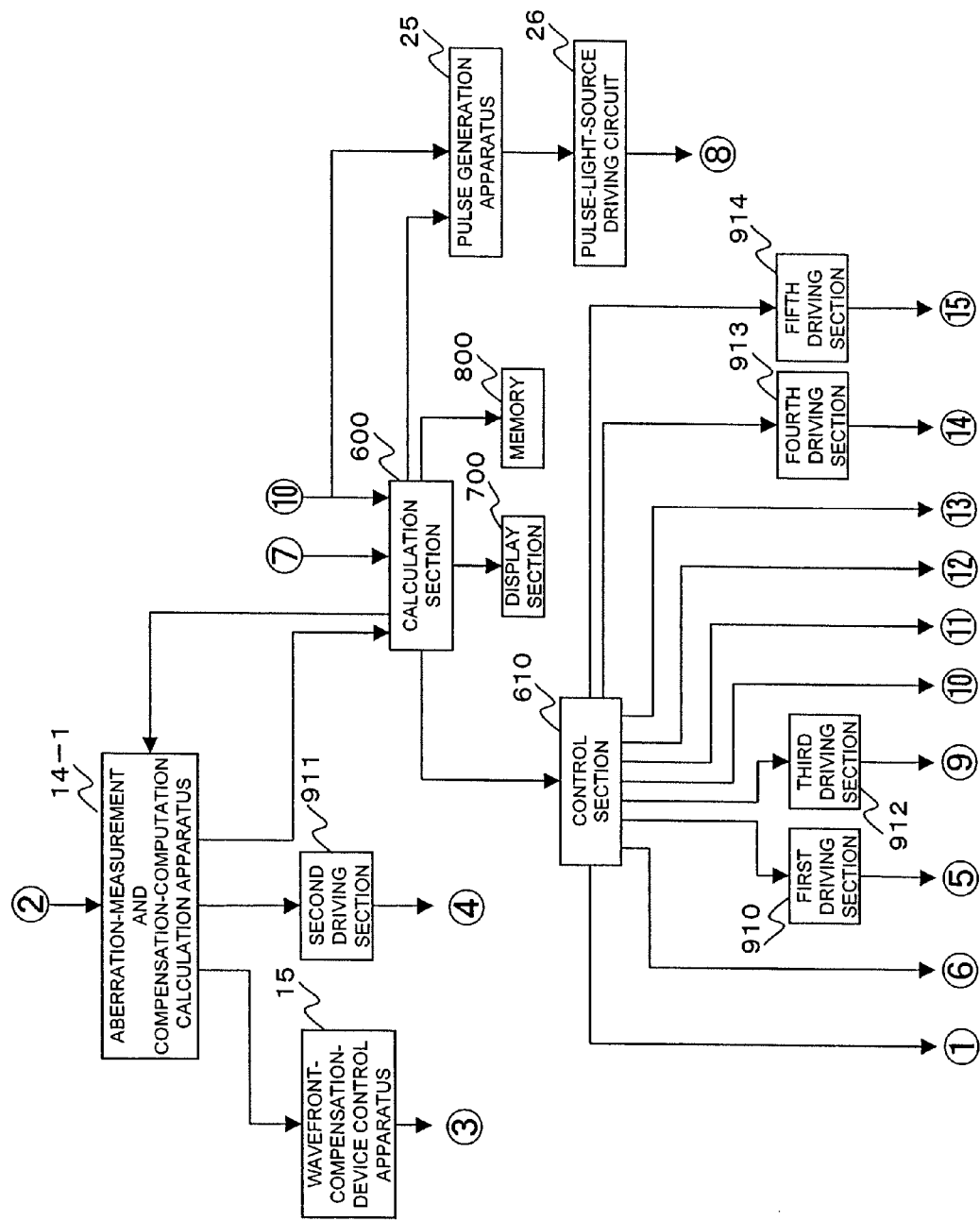
FIG. 12 is a block diagram of an electrical system in the second embodiment.

FIG. 11 is a view showing signals in the second embodiment. FIG. 12 is a block diagram of an electrical system of the second embodiment.

In the structure of the electrical system of the present embodiment, a calculation section 600, a control section 610, a display section 700, a memory 800, a first driving section 910, a second driving section 911, a third driving section 912, a fourth driving section 913, and a fifth driving section 914 are provided. The ophthalmologic imaging apparatus may further include an input section. The same parts as in the first embodiment are assigned the same symbols as those in the first embodiment, and a description thereof is omitted.

The control section 610 further outputs a signal (12) and a signal (13) to the optical switches 34. The fourth driving section 913, for example, outputs a signal (14) to drive a unit for moving the focusing lens 35 to move the focusing lens 35 along the optical axis. The fifth driving section 914, for example, outputs a signal (15) to drive a unit for moving the fixation target 52 to move the fixation target 52 perpendicularly to the optical axis. By moving the fixation target 52 perpendicularly to the optical axis, it is possible to bring a desired portion on the retina to the center of the image.

2.4 Operation

Figure 13:
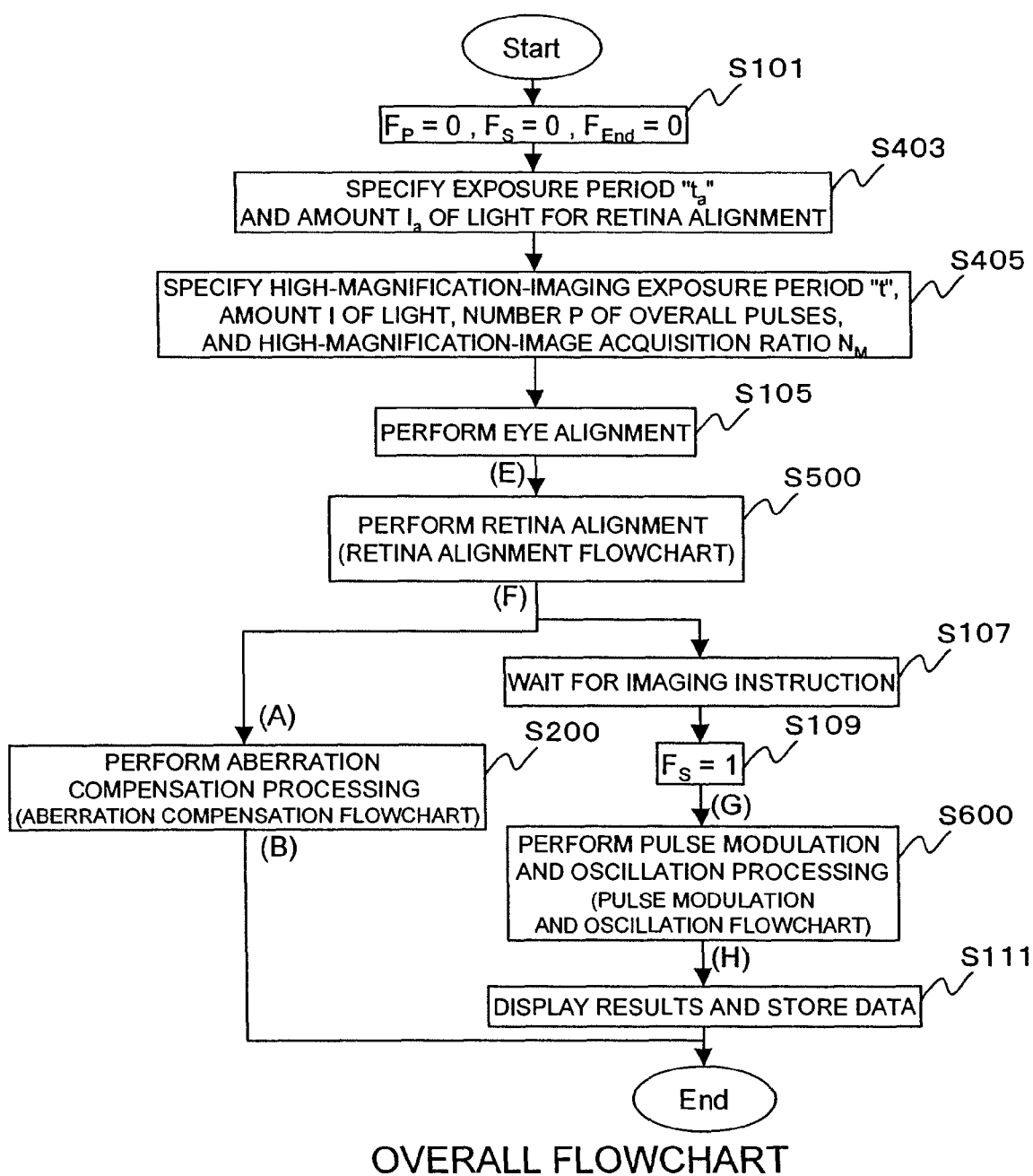
FIG. 13 is an overall flowchart in the second embodiment.

FIG. 13 is an overall flowchart in the second embodiment. The same parts as in the first embodiment are assigned the same symbols as those in the first embodiment, and a description thereof is omitted.

The calculation section 600 first specifies initial settings in step S101. For example, the calculation section 600 sets a flag $F_P$ to zero, a flag $F_S$ to zero, and a flag $F_{End}$ to zero. Next, the calculation section 600 specifies an exposure period "$t_a$" and the amount $I_a$ of light for retina alignment in step S403. The exposure period "$t_a$" and the amount $I_a$ of light may be input from an appropriate input apparatus, or values thereof stored in advance in the memory 800 may be read. The exposure period "$t_a$" and the amount $I_a$ of light are also for low-magnification images. The calculation section 600 specifies a high-magnification-imaging exposure period "t", the amount I of light, the number P of overall pulses, and a high-magnification-image acquisition ratio $N_M$ in step S405. The high-magnification-imaging exposure period "t", the amount I of light, the number P of overall pulses, and the high-magnification-image acquisition ratio $N_M$ may be input from an appropriate input apparatus, or values thereof stored in advance in the memory 800 may be read.

The number P of overall pulses indicates, for example, the number of overall pulses output from the pulse light source 21. This indicates, for example, how many images will be taken, including high-magnification retina images and low-magnification retina images. The high-magnification-image acquisition ratio $N_M$ is set to two when high-magnification images and low-magnification images are to be taken at a ratio of 2:1. Then, the calculation section 600 performs eye alignment in step S105.

The calculation section 600 performs retina alignment in step S500. Details of retina alignment will be described later with reference to a retina alignment flowchart. Then, the calculation apparatus 14-1 performs aberration compensation processing in step S200. Details of the aberration compensation processing are as described above. The calculation section 600 performs the following processes in parallel to step S200.

The calculation section 600 waits for an imaging instruction in step S107. The calculation section 600 sets the flag $F_S$ to "1" according to an imaging instruction in step S109. Then, the calculation section 600 performs pulse modulation and oscillation processing in step S600. Details of the pulse modulation and oscillation processing will be described later with reference to a pulse modulation and oscillation flowchart. The calculation section 600 displays data that includes a plurality of retina images obtained in the pulse modulation and oscillation processing, on the display section 700 in step S111.

Figure 14:
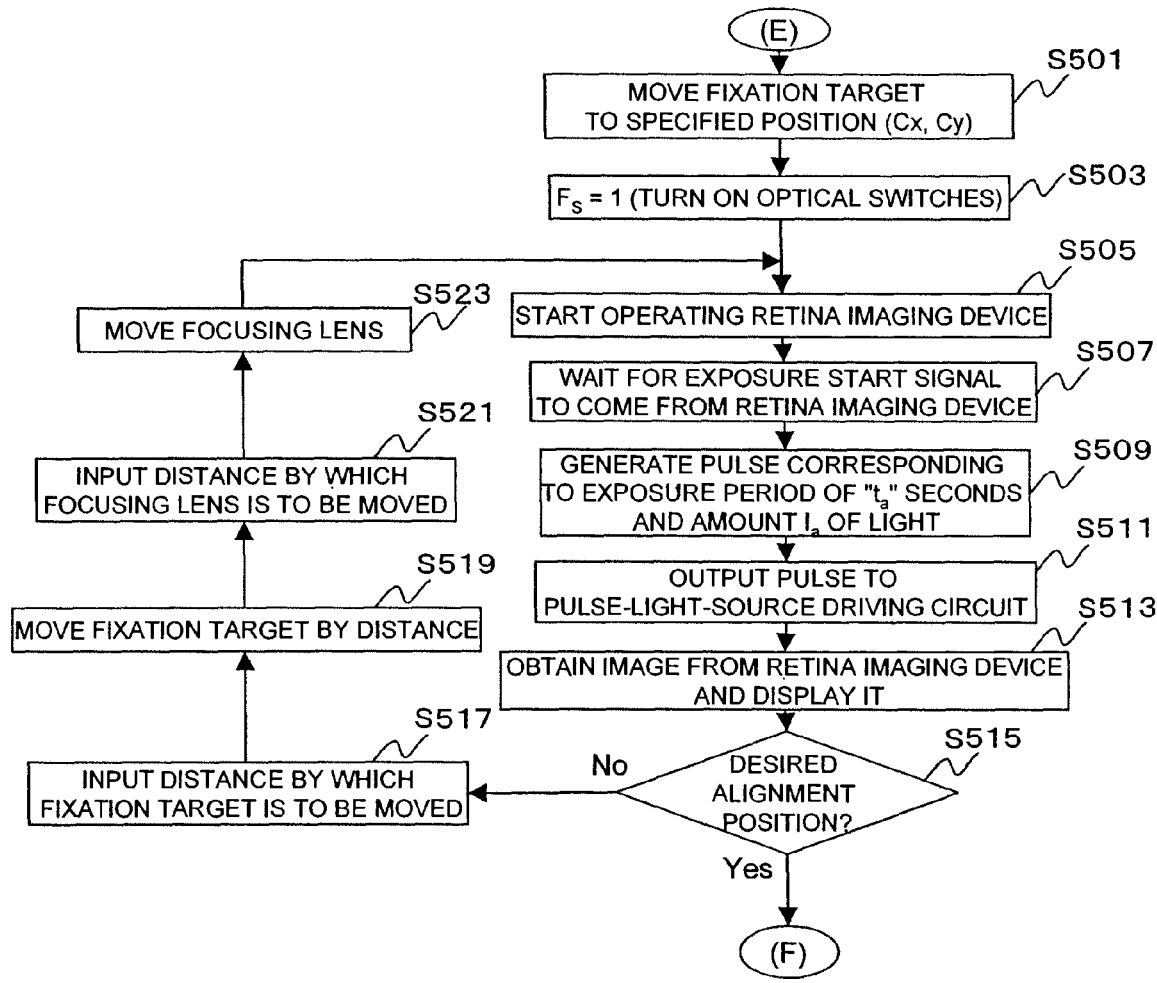
FIG. 14 is a flowchart of retina alignment.
Figure 18:
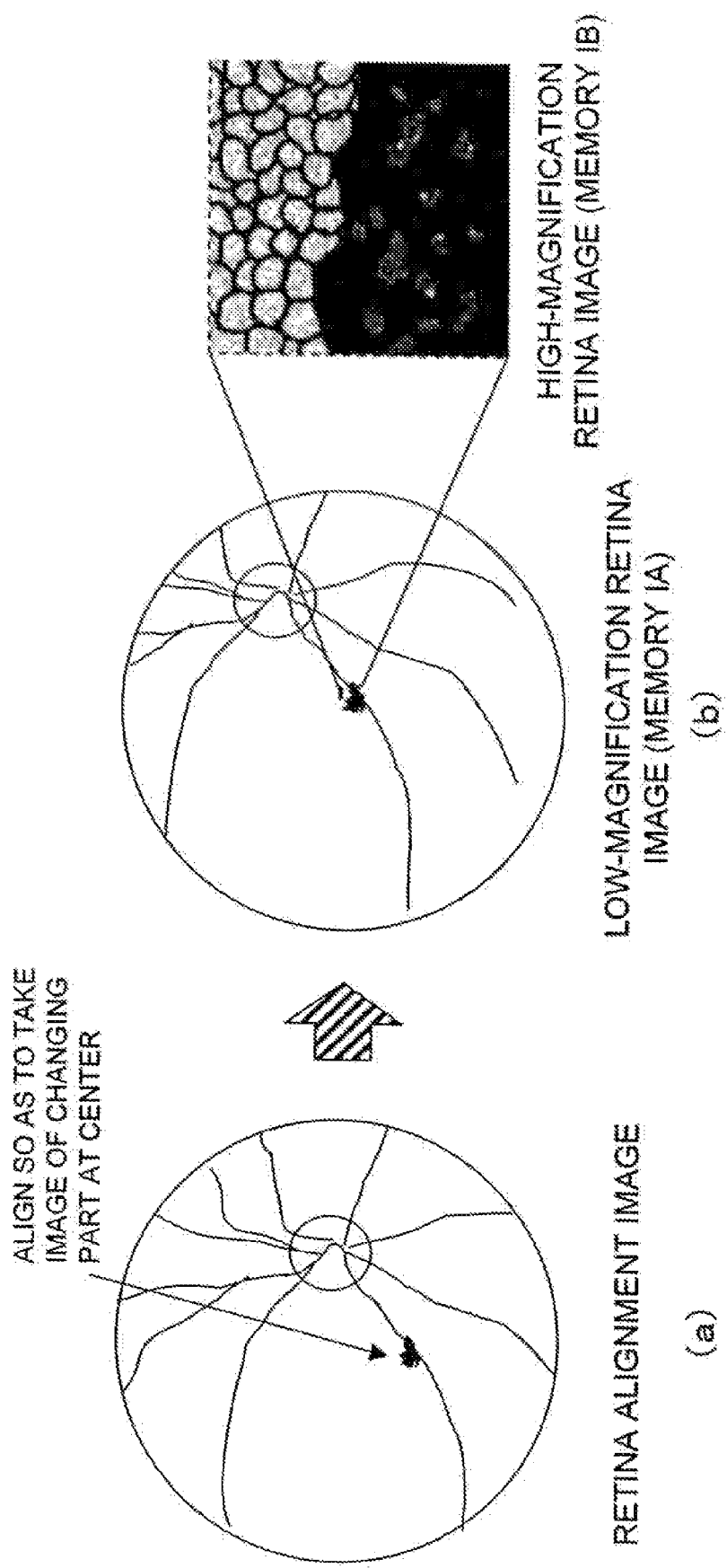
FIG. 18 is a view showing retina alignment.

FIG. 14 is the retina alignment flowchart, which is a detailed flowchart of step S500, described above. FIG. 18 is a view showing retina alignment.

The calculation section 600 first drives the fifth driving section 914 through the control section 610 to move the fixation target 52 to a specified position (Cx, Cy) in step S501. At this time, the imaging center of the eye (eyeground, retina, or others) under measurement is (Cx/ρ, Cy/ρ), where ρ indicates the magnification between the fixation target 52 and the eye (eyeground, retina, or others) under measurement. Cx and Cy can be values specified in advance. The calculation section 600 also sets the optical switches 34 on ($F_S$=1) through the control section 610 in step S503. In the present embodiment, the flag $F_S$ is used, for example, to identify the state of the optical switches 34. When the flag $F_S$ is "1", it means that the optical switches 34 are on; and when the flag $F_S$ is "0", it means that the optical switches 34 are off. When the optical switches 34 are set on, a light beam reflected from the eye under measurement passes through the low-magnification optical path p.

Then, the calculation section 600 starts the operation of the retina imaging device 32 through the control section 610 in step S505. The calculation section 600 waits for an exposure start signal to come from the retina imaging device 32 in step S507. When the calculation section 600 receives an exposure start signal, the pulse generation apparatus 25 generates a pulse corresponding to the specified exposure period, "$t_a$" seconds, and the amount $I_a$ of light for eye alignment in step S509. Then, the pulse generation apparatus 25 outputs the generated pulse to the pulse-light-source driving circuit 26 in step S511. The pulse light source 21 emits pulse light corresponding to the pulse generated in step S509, under the control of the pulse-light-source driving circuit 26.

When exposure has been performed for the specified retina-alignment exposure period, "$t_a$" seconds, the calculation section 600 reads data that includes a retina image from the retina imaging device 32 and displays the data on the display section 700 in step S513. FIG. 18(a) shows a display example. Then, the calculation section 600 determines in step S515 whether alignment with a desired position has been performed or not. For example, it is possible that the operator views the retina image displayed on the display section 700 and inputs whether alignment with the desired position has been performed, at an appropriate input apparatus, and the calculation section 600 determines according to the input signal whether alignment with the desired position has been performed.

If the desired alignment position is not obtained in step S515, the calculation section 600 inputs the distance by which the fixation target 52 is to be moved, at an appropriate input apparatus or the like in step S517. For example, the distance by which the fixation target 52 is to be moved may be input, or the mouse or the like is clicked at the desired position on the image displayed on the display section 700 to obtain the distance by which the image center is shifted to the clicked position. For example, alignment can be performed such that an image is to be taken with a changing part such as a blood vessel at the center. The calculation section 600 drives the fifth driving section 914 through the control section 610 to move the fixation target 52 in step S519 by the distance input in step S517.

Then, the calculation section 600 inputs the distance by which the focusing lens 35 is to be moved, at an appropriate input apparatus in step S521. The focusing lens 35 can be moved by a desired distance to adjust the focus when the fixation target is moved, or to adjust the retina alignment along the optical axis. The distance may be specified from an obtained image such that the maximum contrast is obtained near the desired portion on the image. Then, the calculation section 600 uses the control section 610 to drive the fifth driving section 914 to move the focusing lens 35 in step S523 by the distance input in step S521. The processing proceeds to step S505, and the processes in step S505 to step S515 are repeated. By moving the fixation target 52 and the focusing lens 35, the eye is moved, the desired portion comes to the center, and the focus is at the desired position. FIG. 18(b) shows a retina image obtained when the desired portion came to the center. A center area can be captured at a high magnification to observe the desired portion in the high-magnification retina image in detail.

When the desired alignment position is obtained in step S515, the calculation section 600 terminates the retina alignment processing (go to (F) in FIG. 14).

Figure 15:
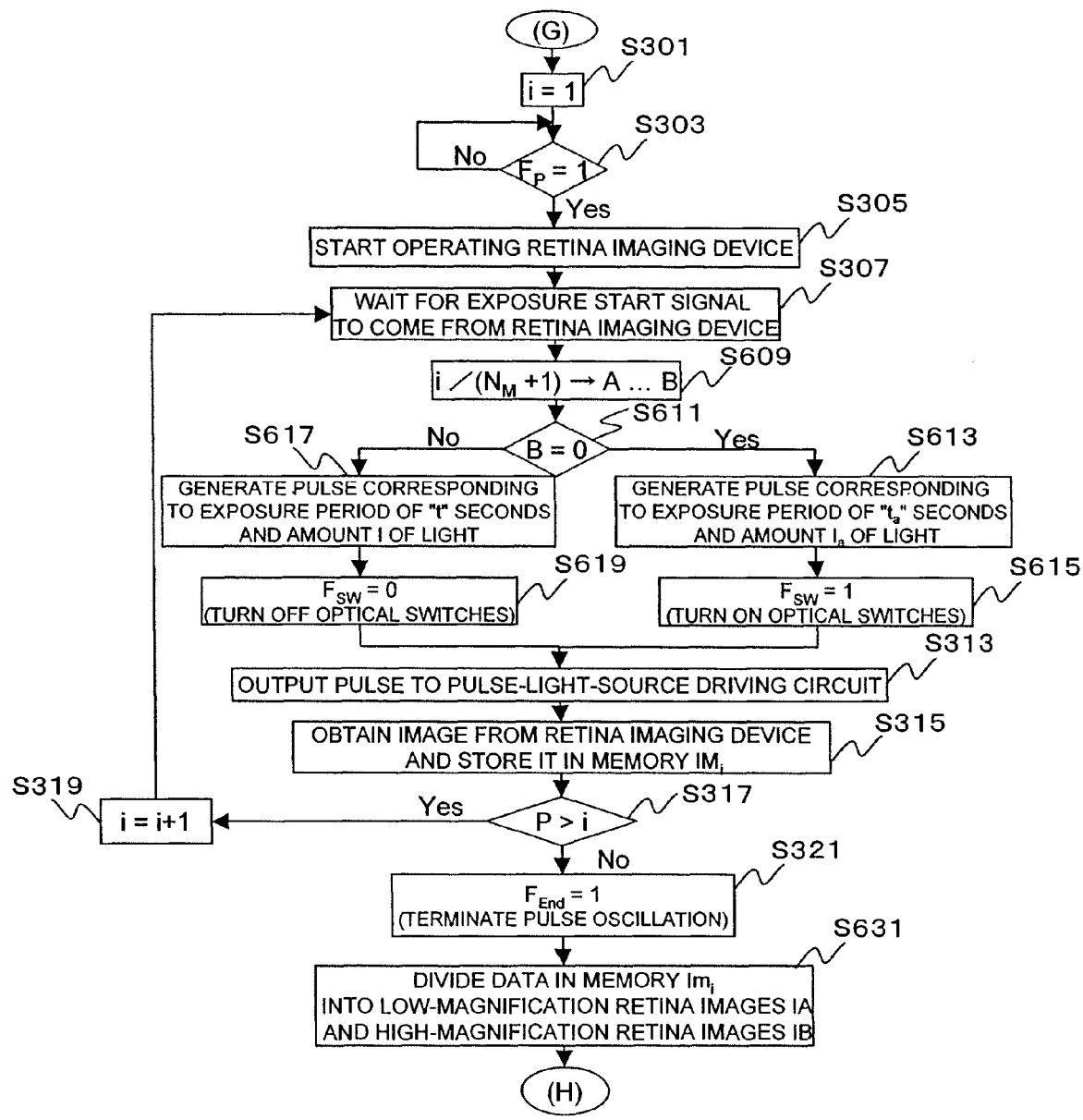
FIG. 15 is a first flowchart of pulse modulation and oscillation.

FIG. 15 is a first flowchart of pulse modulation and oscillation, which is a detailed flowchart of step S600, described above. In the flowchart, high-magnification images and low-magnification images are obtained at a ratio determined in advance. The same processes as those shown in the above flowchart are assigned the same symbols as those used in the above flowchart, and a detailed description thereof is omitted.

The calculation section 600 first executes the processes in step S301 to step S307. Then, the calculation section 600 determines whether to obtain a high-magnification retina image or a low-magnification retina image in steps S609 and S611. In the present case, for example, from the parameter "i" and the high-magnification-image acquisition ration $N_M$, $i/(N_M+1)$ is calculated and the quotient is called A and the remainder is called B in step S609. When the remainder obtained in step S609 is zero (B=0), the processing proceeds to step S613; and when B is not zero, the processing proceeds to step S617. In other words, when B is zero (Yes in step S611), the processing proceeds to processes for obtaining a low-magnification image; and when B is not zero (No in step S611), the processing proceeds to processes for obtaining a high-magnification image. The processes for determining whether to obtain a low-magnification image or a high-magnification image may use an appropriate method other than that described above.

In step S613, the pulse generation apparatus 25 generates a pulse corresponding to a specified exposure period of "$t_a$" seconds and the amount $I_a$ of light. Then, the calculation section 600 (image-acquisition control PC 14-4) uses the control section 610 to turn on the optical switches 34 ($F_{SW}$=1) in step S615. In the present case, when the optical switches 34 are turned on, a light beam coming from the eye under measurement passes through the low-magnification optical path β and is received by the retina imaging device 32.

In contrast, in step S617, the pulse generation apparatus 25 generates a pulse corresponding to a specified exposure period of "t" seconds and the amount I of light. Then, the calculation section 600 (image-acquisition control PC 14-4) uses the control section 610 to turn off the optical switches 34 ($F_{SW}$=0) in step S619. In the present case, when the optical switches 34 are turned off, a light beam coming from the eye under measurement passes through the high-magnification optical path α and is received by the retina imaging device 32.

When the optical switches 34 are switched, the pulse generation apparatus 25 outputs the generated pulse to the pulse-light-source driving circuit 26 in step 313. The second embodiment may be configured such that the image-acquisition control PC 14-4 outputs a signal indicating that the optical switches have been switched, to the pulse generation apparatus 25 and the pulse generation apparatus 25 executes the process of step S313 in response to the signal. The pulse light source 21 is driven by the pulse-light-source driving circuit 26 to emit pulse light corresponding to the pulse generated in step S613 or step S617. Next, when exposure is performed for the specified exposure period, "t" or "$t_a$" seconds, the calculation section 600 reads data such as a retina image from the retina imaging device 32 and stores it in the memory 800 as data $IM_i$ corresponding to the parameter "i" in step S315. The time and the value of the flag $F_{SW}$ may be further stored. Then, the calculation section 600 executes the processes of steps S317, S319, and S321. After step S321, the calculation section 600 divides the data $IM_i$ corresponding to the parameter "i", stored in the memory 800, into low-magnification retina images IA and high-magnification retina images IB in step S631, and terminates the processing of pulse modulation and oscillation (go to (H) in the figure). In step S315, low-magnification images and high-magnification images may be separately stored with the use, for example, of the value of the flag $F_{SW}$ to omit step S631.

Figure 16:
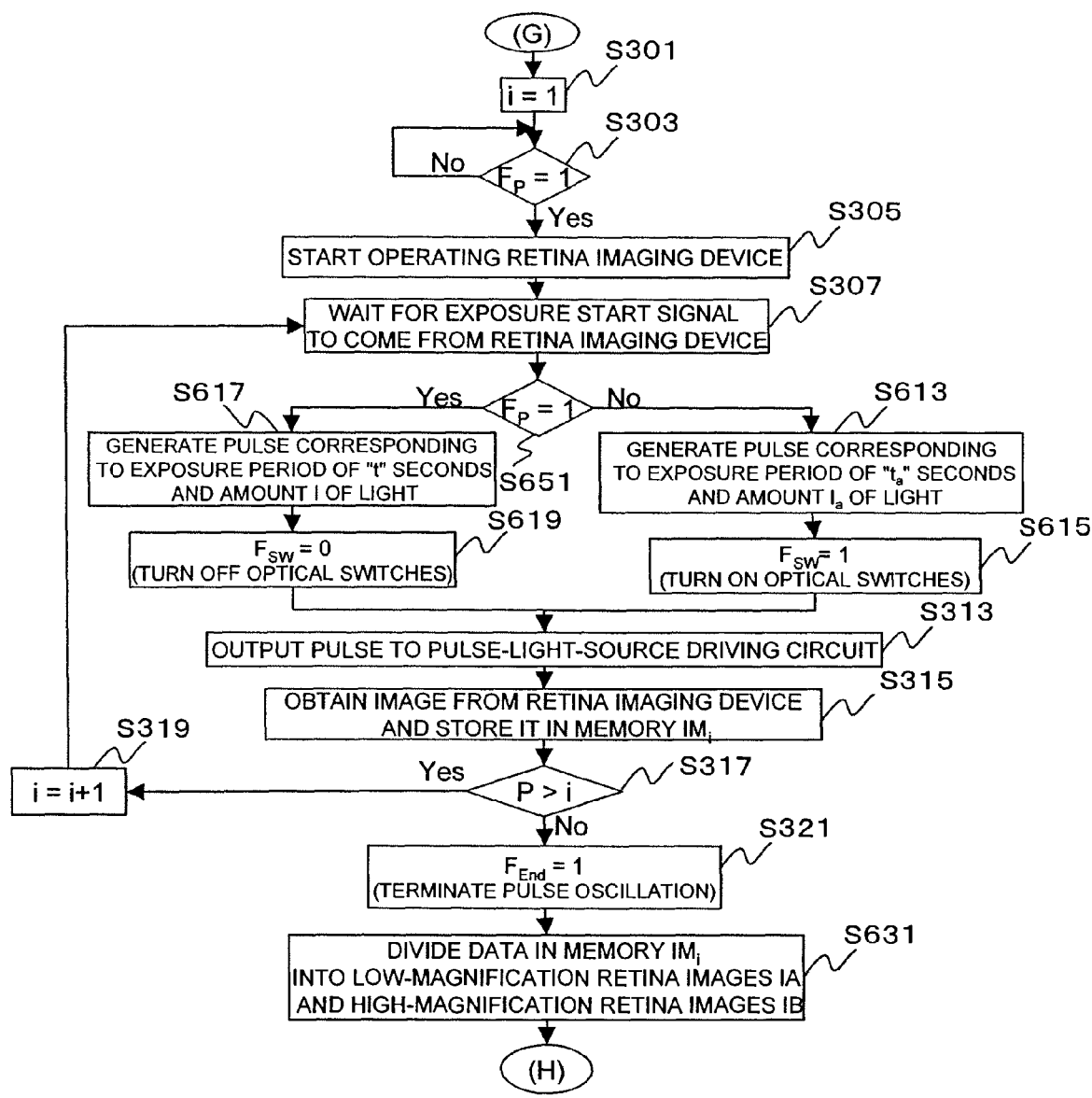
FIG. 16 is a second flowchart of pulse modulation and oscillation, used in a case where the magnification is changed according to the amount of aberrations.

FIG. 16 shows a second flowchart of pulse modulation and oscillation, which is a another detailed flowchart of step S600, described above. In the present flowchart, the magnification is changed according to the amount of aberrations. For example, when the amount of aberrations is large, a low-magnification image is obtained; and when the amount of aberrations is small, a high-magnification image is obtained. In this way, frames are not wasted and a quality image is obtained. In addition, the measurement time is reduced. The same processes as those in the first flowchart of pulse modulation and oscillation, described above, are assigned the same symbols as those used in the first flowchart, and a description thereof is omitted.

The calculation section 600 first executes the processes in step S301 to step S307. Then, the calculation section 600 determines in step S651 whether to obtain a high-magnification retina image or a low-magnification retina images according to the result of the aberration measurement performed in parallel to the processing of pulse modulation and oscillation. In the present case, for example, when the amount of aberrations is larger than a threshold, a low-magnification image is obtained; and when the amount of aberrations is sufficiently small, a high-magnification image is obtained. For example, the calculation section 600 determines whether the flag $F_P$ is equal to "1" or not. When the flag $F_P$ is equal to "1" (Yes in step S651), the processing proceeds to step S617. When the flag $F_P$ is not equal to "1" (No in step S651), the processing proceeds to step S613. The calculation section executes the process of step S613 or S617 and those of subsequent steps.

FIG. 17A and FIG. 17B are timing charts in the second embodiment.

FIG. 17A is a timing chart for retina alignment. FIG. 17B is a timing chart for consecutive image acquisition at $N_M$ being set to "2". When the optical switches 34 is on ($F_{SW}$="1"), a low-magnification pulse is sent. In the present case, since the identical optical system of the retina illumination system 2 is used, a laser output is made higher for high-magnification imaging to obtain brightness levels close to each other between the high-magnification system and the low-magnification system. In theory, when the magnification is "k", "$k^2$" times the amount of light is required.

3. Modification of second embodiment

In the second embodiment, two light sources may be used to obtain retina images, one for high-magnification images and the other for low-magnification images. A timing chart and an optical system for that case will be described below.

Figure 19:
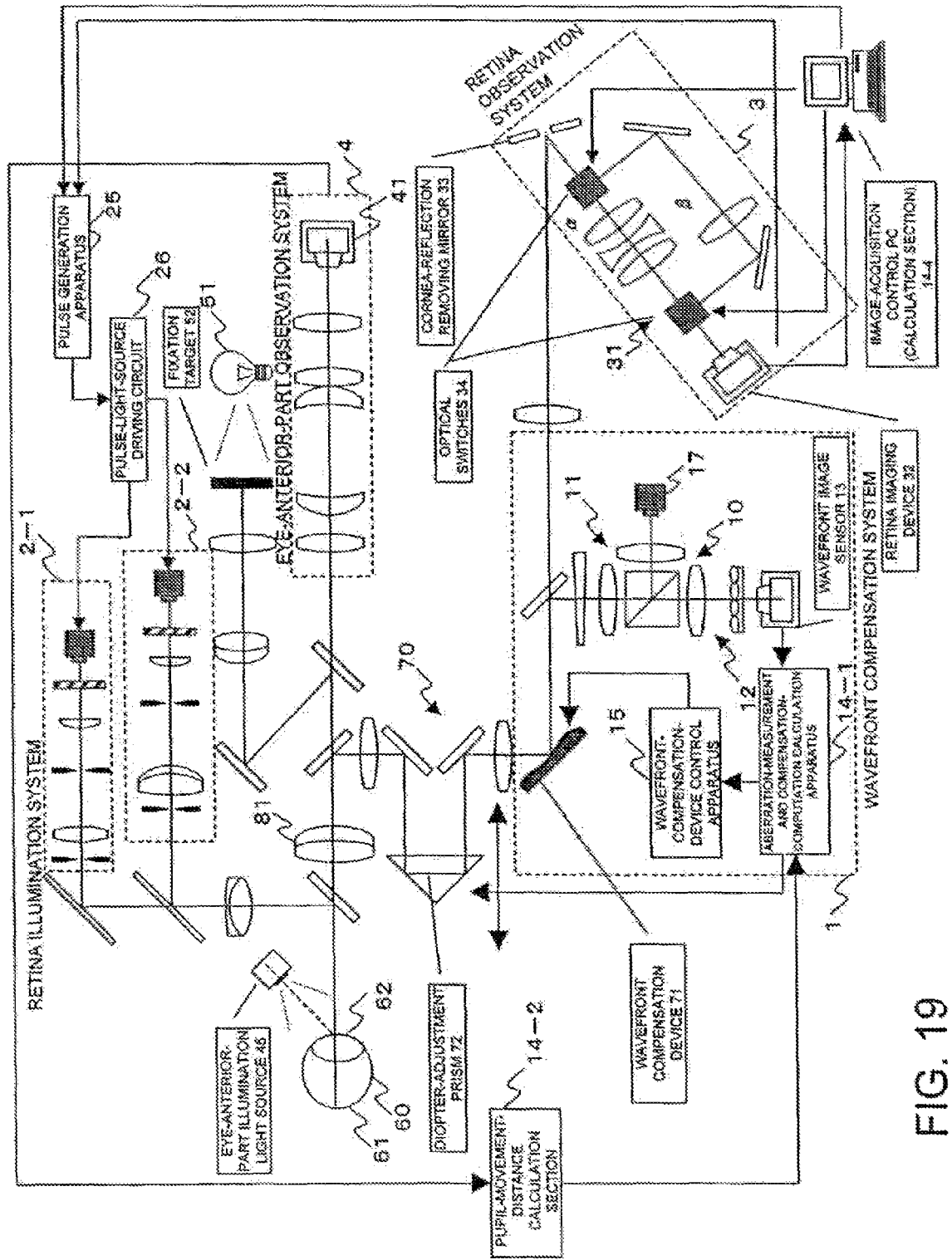
FIG. 19 is a view showing the optical arrangement of a third embodiment.

FIG. 19 is a view showing an optical arrangement where two light sources are used.

The same components as those used in the second embodiment are assigned the same symbols, and a description thereof is omitted. A retina illumination system 2 has a high-magnification illumination system and a low-magnification illumination system. For example, in the figure, an illumination system 2-1 is used for a high magnification and an illumination system 2-2 is used for a low magnification. Since illumination for the high magnification and illumination for the low magnification are separately provided in this structure, different aperture diaphragms and different viewing-field diaphragms can be used to eliminate an unnecessary illumination area and to reduce a load imposed on the eye under measurement. In addition, since the amount of light emitted from each light source can be set constant, fluctuations in the wavelength and output of each light source, caused by changes in temperature are also reduced. When a pulse-light-source driving circuit 26 receives a high-magnification pulse from a pulse generation apparatus 25, the pulse-light-source driving circuit 26 drives the high-magnification pulse light source; and when the pulse-light-source driving circuit 26 receives a low-magnification pulse from the pulse generation apparatus 25, the pulse-light-source driving circuit 26 drives the low-magnification pulse light source. For example, the pulse-light-source driving circuit 26 may receive a flag $F_{SW}$ indicating the on or off state of optical switches from a calculation section 600 (image-acquisition control PC 14-4) to switch the output between the high-magnification pulse light source and the low-magnification pulse light source according to the flag.

Figure 20:
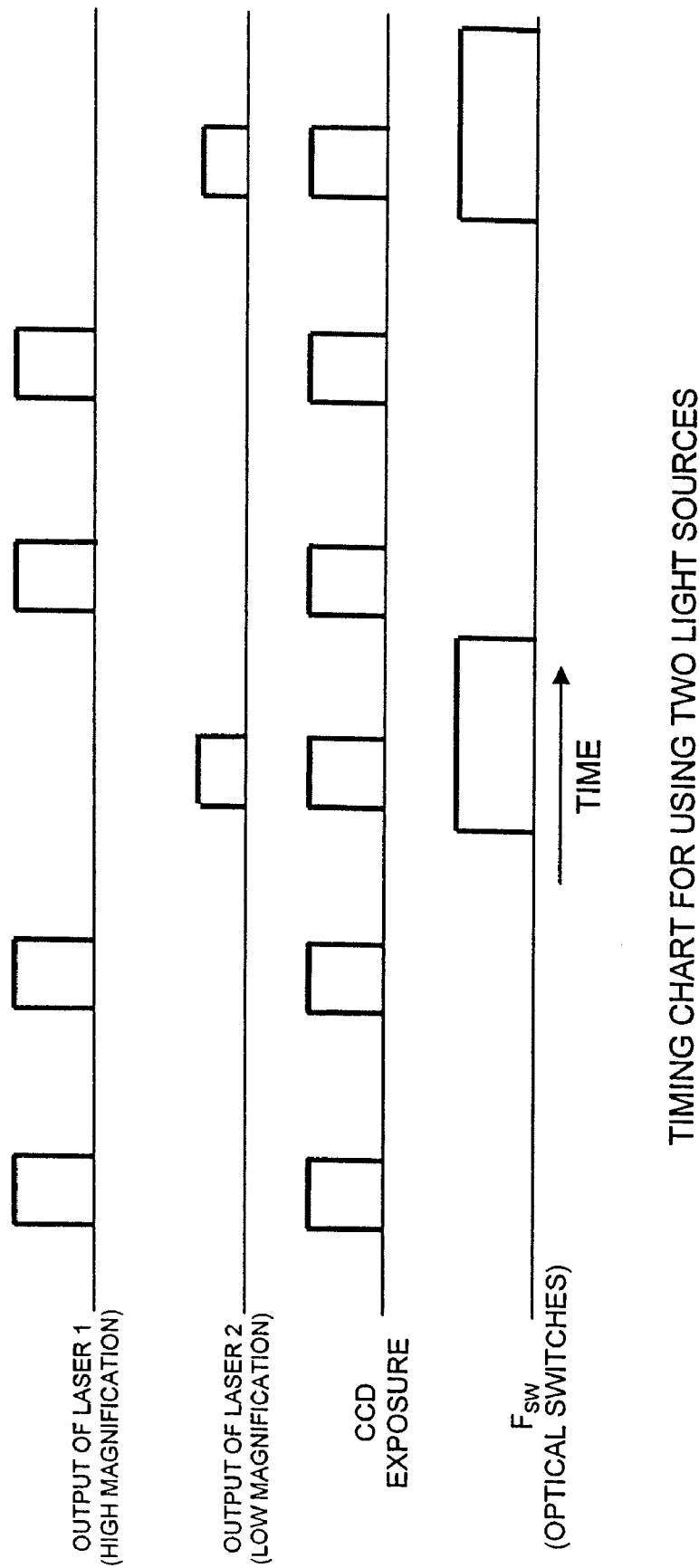
FIG. 20 is a timing chart in the third embodiment.

FIG. 20 is a timing chart for a case where two light sources are used. For example, a high-magnification laser and a low-magnification laser separately output high-magnification pulses and low-magnification pulses.

The present invention can be used, for example, for retina-image imaging apparatuses in ophthalmology.

What is claimed is:

1. An ophthalmologic imaging apparatus comprising:
a light source section for emitting a pulse light at predetermined timing;
an illumination optical system for illuminating a retina of an eye under measurement, with the pulse light emitted from the light source section;
an aberration compensation section for applying compensation to a light beam reflected from the retina so as to cancel out at least high-order aberrations, according to measured aberrations;
an aberration measurement section for illuminating the eye under measurement, for receiving a light beam reflected from the eye under measurement when illuminated, through the aberration compensation section, and for measuring aberrations in the light beam reflected;
a light-receiving section for receiving a light beam coming from the retina to form an image; and
a light-receiving optical system for forming a retina image on the light-receiving section with a light beam of the light source section, which was reflected from the retina and of which aberrations have been compensated for by the aberration compensation section, wherein the light-receiving optical system comprises a variable-magnification section for changing the magnification of the retina image formed on the light-receiving section;

the light-receiving optical system uses the variable-magnification section to be capable of switching at least between a high-magnification mode and a low-magnification mode;

the light-receiving optical system is configured such that the mode is switched to the high-magnification mode when the aberrations measured by the aberration measurement section are equal to or smaller than aberrations determined in advance, and the mode is switched to the low-magnification mode when the aberrations measured by the aberration measurement section are larger than the aberrations determined in advance; and the light source section emits a plurality of pulse lights at each exposure timing when the light-receiving section is exposed to light a plurality of times and the light-receiving section obtains consecutive retina images.

2. An ophthalmologic imaging apparatus according to claim 1, wherein the aberration measurement section periodically measures the aberrations;

the aberration compensation section periodically compensates for the aberrations according to the measured aberrations; and the light source section emits a light at the exposure timing of the light-receiving section when the aberrations measured by the aberration measurement section are smaller than aberrations determined in advance.

3. An ophthalmologic imaging apparatus according to claim 1, wherein the variable-magnification section comprises:

a low-magnification optical path for forming the retina image on the light-receiving section at a first magnification;

a high-magnification optical path for forming the retina image on the light-receiving section at a second magnification higher than the first magnification; and an optical switch for switching the optical path of the pulse light reflected by the retina to either the low-magnification optical path or the high-magnification optical path.

4. An ophthalmologic imaging apparatus according to claim 1, wherein the variable-magnification section is used to switch the magnification to a first magnification and the retina image is obtained;

a desired position or a desired area is selected in the obtained retina image;

a fixation target which the eye under measurement observes is moved in a two-dimensional plane perpendicular to the optical axis such that the desired position or the desired area comes close to the center of a retina image; and the variable-magnification section is used to switch to a second magnification which is higher than the first magnification, and a retina image that includes the desired position or the desired area is obtained at the second magnification.

5. An ophthalmologic imaging apparatus according to claim 1, wherein the amount of light of a first pulse light for obtaining a retina image at a high magnification and the amount of light of a second pulse light for obtaining a retina image at a low magnification are adjusted such that the obtained retina images have the same brightness or almost the same brightness.

6. An ophthalmologic imaging apparatus according to claim 1, further comprising a display section for displaying a plurality of retina images received by the light-receiving section.

7. An ophthalmologic imaging apparatus according to claim 1, wherein the light source section further emits a pulse light between pulse light emitted according to exposure timing for obtaining retina images.

* * * * *